United States Patent
Fu et al.

(10) Patent No.: US 10,933,144 B2
(45) Date of Patent: *Mar. 2, 2021

(54) NON-LINEAR MULTIBLOCK COPOLYMER-DRUG CONJUGATES FOR THE DELIVERY OF ACTIVE AGENTS

(71) Applicant: The Johns Hopkins University, Baltimore, MD (US)

(72) Inventors: Jie Fu, Baltimore, MD (US); Peter A. Campochiaro, Baltimore, MD (US); Justin Scot Hanes, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/182,261

(22) Filed: Nov. 6, 2018

(65) Prior Publication Data

US 2019/0070302 A1 Mar. 7, 2019

Related U.S. Application Data

(63) Continuation of application No. 13/797,531, filed on Mar. 12, 2013, now Pat. No. 10,159,743.

(60) Provisional application No. 61/611,975, filed on Mar. 16, 2012.

(51) Int. Cl.
| | | |
|---|---|---|
| *A61K 47/59* | (2017.01) | |
| *A61K 47/60* | (2017.01) | |
| *A61K 47/69* | (2017.01) | |
| *A61K 47/68* | (2017.01) | |

(52) U.S. Cl.
CPC .............. *A61K 47/60* (2017.08); *A61K 47/59* (2017.08); *A61K 47/6827* (2017.08); *A61K 47/6927* (2017.08); *A61K 47/6957* (2017.08)

(58) Field of Classification Search
CPC .... A61K 47/60; A61K 47/59; A61K 47/6927; A61K 47/6957; A61K 47/6827
See application file for complete search history.

(56) References Cited

U.S. PATENT DOCUMENTS 10,159,743 B2 * 12/2018 Fu et al.
2011/0262490 A1 * 10/2011 Zhang

OTHER PUBLICATIONS

Lee Tong De, "Synthesis and Characterization of biodegradable polymer material", Full-text Database of Thesis from China's Outstanding Master's Degree, Engineering Science, Series 1, 4:B016-44 (2008), pp. 6-8.

* cited by examiner

*Primary Examiner* — Alma Pipic
(74) *Attorney, Agent, or Firm* — Pabst Patent Group LLP

(57) ABSTRACT

Non-linear multiblock copolymer-drug conjugates for the treatment and prevention of diseases and disorders of the eye are provided. The polymer-drug conjugates can form nanoparticles, microparticles, and implants that are capable of effectively delivering therapeutic levels of one or more active agents for an extended period of time. Administration to the eye of an active agent in the form of a non-linear multiblock copolymer-drug conjugate produces decreased side effects when compared to administration of the active agent alone. Also provided are methods of treating intraocular neovascular diseases, such as wet age-related macular degeneration as well as diseases and disorders of the eye associated with inflammation, such as uveitis.

26 Claims, 9 Drawing Sheets

NON-LINEAR MULTIBLOCK COPOLYMER-DRUG CONJUGATES FOR THE DELIVERY OF ACTIVE AGENTS

CROSS REFERENCE TO RELATED APPLICATION

This application is a continuation of U.S. application Ser. No. 13/797,531, filed Mar. 12, 2013, which claims benefit of U.S. Provisional Application No. 61/611,975 filed Mar. 16, 2012, which are herein incorporated by reference in their entirety.

STATEMENT REGARDING FEDERALLY SPONSORED RESEARCH OR DEVELOPMENT

This invention was made with Government Support under Agreements R01CA140746, P30EY001765, and U54CA151838 awarded to Justin Scot Hanes by the National Institutes of Health, and under Agreement R01EY012609 awarded to Peter Anthony Campochiaro by the National Institutes of Health. The Government has certain rights in the invention.

FIELD OF THE INVENTION

The present invention relates to non-linear multiblock copolymer-drug conjugates with improved efficacy, stability, safety and ease of formation into nano- and microparticles, as well as methods of use thereof for the controlled delivery of active agents, particularly for the controlled delivery of active agents to the eye.

BACKGROUND OF THE INVENTION

Approximately 1.7 million Americans over the age of 65 suffer from age-related macular degeneration (AMD). As the nation's population continues to age, this number is expected to grow by an estimated 200,000 new cases per year. Severe vision loss from AMD and other diseases affecting the posterior segment, including diabetic retinopathy, glaucoma, and retinitis pigmentosa accounts for most cases of irreversible blindness worldwide.

Currently, the treatment of posterior segment diseases is to a significant extent limited by the difficulty in delivering effective doses of drugs to target tissues in the posterior eye while avoiding toxicity. Four modes of administration are commonly used to deliver drugs to the posterior segment of the eye: topical, systemic, intraocular, and periocular administration.

Topical administration, for example the application of solutions to the surface of the eye, is the most common mode of administration of therapeutics for the pharmacologic management of ocular disease. Topical administration has the advantage of being minimally invasive; however, many factors can limit its usefulness. Examples include the significant barrier to solute flux provided by the corneal epithelium, and the rapid and extensive precorneal loss that occurs as the result of drainage and tear fluid turnover. It has been estimated that typically less than 5% of a topically applied drug permeates the cornea and reaches intraocular tissues. The major portion of the instilled dose is absorbed systemically by way of the conjunctiva, through the highly vascular conjunctival stroma and through the lid margin vessels. Significant systemic absorption also occurs when the solution enters the nasolacrimal duct and is absorbed by the nasal and nasopharyngeal mucosa. Despite the relatively small proportion of a topically applied drug dose that ultimately reaches anterior segment ocular tissues, topical formulations can be effective in some circumstances, largely because of the very high concentrations of drugs that can be administered.

Recent advances in topical drug delivery have focused on improving ocular drug contact time and drug delivery from the surface of the eye to the posterior segment. For example, ointments, gels, liposome formulations, and various sustained and controlled-release substrates, such as the Ocusert® system, collagen shields, and hydrogel lenses, have been developed to improve ocular drug contact time. Topical delivery systems using polymeric gels, colloidal systems, and cyclodextrins have also been investigated in an effort to improve drug delivery to the posterior segment. In spite of these efforts, the delivery of therapeutic doses of drugs to the posterior segment of the eye by topical routes remains a significant challenge.

Drugs for the treatment of posterior segment diseases can also be administered systemically. Although systemic administration can deliver drugs to the posterior eye, large systemic doses are typically required to yield therapeutic drug levels in the posterior vitreous, retina, or choroid. As a result, systemic administration is generally plagued by significant side effects associated with the administration of large systemic doses of the therapeutic agent.

Periocular drug delivery using subconjunctival or retrobulbal injections or placement of sustained-release devices provides another route for delivering drugs to the posterior tissues of the eye. This approach offers the potential for localized, sustained-release drug delivery. The average 17 $cm^2$ surface area of the human sclera accounts for 95% of the total surface area of the globe and provides a significantly larger avenue for drug diffusion to the inside of the eye than the 1-$cm^2$ surface area of the cornea. Also, regional differences in scleral thickness could be used to further optimize transscleral drug diffusion if sustained-release delivery devices or systems could be placed in regions where scleral permeability was greatest. The sclera, for example, is 1.0 mm thick near the optic nerve and an average of 0.53 mm thick at the corneoscleral limbus and thins to an average of 0.39 mm at the equator, where it can be as thin as 0.1 mm in a significant number of eyes. See Geroski, et al. Invest. Ophthalmol. Vis. Sci. 41(5):961-964 (2000).

Intravitreal injection represents the most common method for administering therapeutic drug levels to the posterior segment of the eye. While intravitreal injection offers the opportunity to control initial drug levels in the posterior segment of the eye while minimizing any systemic toxicity associated with the drug, intravitreal administration suffers some significant drawbacks. Intravitreal injections have several inherent potential side effects, including a risk of retinal detachment, hemorrhage, endophthalmitis, and cataract development. Repeat injections are frequently required, and they are not always well tolerated by the patient. Further, drugs injected directly into the vitreous are rapidly eliminated, making it difficult to maintain therapeutically effective levels of the drug in the posterior segment.

For drugs that are administered to regions of the body where they are rapidly eliminated (e.g., the posterior segment of the eye), are used to treat chronic diseases or disorders, and/or have a narrow therapeutically effective concentration range (i.e., therapeutic window), conventional drug delivery methods are inappropriate. Conventional drug administration involves periodic dosing of a therapeutic agent in a dosage formulation that ensures drug stability, activity, and bioavailability. Administration of the therapeutic agent typically results in a sharp initial increase in drug concentration (often to toxic levels), followed by a steady decline in concentration as the drug is cleared and/or metabolized. To maintain an effective concentration of the therapeutic agent in the posterior segment for the treatment of chronic eye diseases, repeated administration of the dosage formulation is typically required. The periodic drug delivery generates a drug concentration profile that oscillates over time, often spiking to toxic levels and/or dipping below the therapeutic window.

Controlled release formulations offer the potential to improve patient outcomes in these instances. Controlled release formulations provide the ability to minimize/eliminate spikes in drug concentration, minimizing side effects and/or toxicity. Controlled release formulations can also maintain the drug concentration within the therapeutic window for longer periods of time. As a result, these formulations are more comfortable and convenient for the patient, due to a diminished frequency of ocular injections.

Towards this end, intravitreal sustained-release devices have been investigated. The best known of these devices is the VITRASERT™ ganciclovir implant, used in the treatment of cytomegalovirus retinitis. However, implants such as VITRASERT™ require complex and undesirable intraocular surgery, and must be replaced periodically.

Sustained release formulations containing drugs encapsulated in biodegradable polymer particles are an attractive alternative. Nanoparticle and microparticle formulations can be injected as a suspension, obviating the need for intraocular implantation surgeries. As the polymer particles degrade and/or as the drug diffuses out of the polymer particles, the drug is released.

Several drawbacks have hampered the successful development of controlled release polymeric nanoparticle and microparticle formulations. First, it is often difficult to achieve high and/or controlled drug loading during particle formation, particularly for hydrophilic molecules such as doxorubicin. Grovender T. et al. *J. Controlled Release* 57(2):171-185 (1999). Second, it is difficult to achieve high drug encapsulation efficiency when forming polymeric particle, particularly polymeric nanoparticles. Most polymeric particles possess poorly encapsulated drug molecules on or near the particle surface. As a result, many particles display an undesirable biphasic drug release pattern. Upon injection, poorly encapsulated drug molecules on or near the surface of nanoparticles can quickly diffuse into solution, resulting in an initial burst release of drug. In the case of many polymeric nanoparticles, as high as 40-80% of the encapsulated drug molecules are released in a burst during the first several or tens of hours following administration. After the first 24 to 48 hours, drug release becomes significantly slower due to the increased diffusion barrier for drug molecules buried more deeply in polymer particles. Such particles can still produce a sharp initial increase in drug concentration upon administration, often to toxic levels.

Therefore, it is an object of the invention to provide polymer-drug conjugates with improved properties for the controlled delivery of active agents.

It is also an object of the invention to provide drug formulations capable of effectively delivering therapeutic levels of one or more active agents to the eye for an extended period of time.

It is a further object of the invention to provide improved methods of treating or preventing diseases or disorders of the eye.

SUMMARY OF THE INVENTION

Non-linear multiblock copolymer-drug conjugates capable of forming nanoparticles, microparticles, and implants with improved properties for controlled drug delivery, especially to the eye, are provided. The polymer-drug conjugates contain one or more hydrophobic polymer segments and one or more hydrophilic polymer segments covalently connected through a multivalent branch point to form a non-linear multiblock copolymer containing at least three polymeric segments. The polymer-drug conjugates further contain one or more therapeutic, prophylactic, or diagnostic agents covalently attached to the one or more hydrophobic polymer segments. By employing a polymer-drug conjugate, particles can be formed with more controlled drug loading and drug release profiles. In addition, the solubility of the conjugate can be controlled so as to minimize soluble drug concentration and, therefore, toxicity.

The polymer drug conjugates can be represented by the general formula shown below

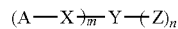

wherein

A represents, independently for each occurrence, an active agent, with the proviso that A is not a HIF-1 inhibitor;

X represents, independently for each occurrence, a hydrophobic polymer segment;

Y represents a multivalent branch point;

Z represents, independently for each occurrence, a hydrophilic polymer segment m is an integer between one and twenty and n is an integer between zero and twenty.

In some embodiments, m is one or greater and n is zero. In other embodiments, m and n are one or greater, such that m+n is 2 or greater, such, 4, or 5 or greater.

Preferably, A is a therapeutic or prophylactic agent that is useful for the treatment or prevention of an ocular disease or disorder, such as an anti-glaucoma agent, anti-angiogenesis agent, anti-infective agent, anti-inflammatory agent, growth factor, immunosuppressant agent, or anti-allergic agent.

The one or more hydrophilic polymer segments can be any hydrophilic, biocompatible, non-toxic polymer or copolymer. In preferred embodiments, the one or more hydrophilic polymer segments contain a poly(alkylene glycol), such as polyethylene glycol (PEG). In preferred embodiments, the polymer-drug conjugates contain more than one hydrophilic polymer segment.

The one or more hydrophobic polymer segments can be any biocompatible, hydrophobic polymer or copolymer. In preferred embodiments, the hydrophobic polymer or copolymer is biodegradable. In preferred embodiments, the hydrophobic polymer is a polyanhydride, such as polysebacic anhydride or a copolymer thereof.

The degradation profile of the one or more hydrophobic polymer segments may be selected to influence the release rate of the active agent in vivo. For example, the hydrophobic polymer segments can be selected to degrade over a time period from several days to 24 weeks, more preferably from seven days to eight weeks, preferably from seven days to three weeks. In other cases, the hydrophobic polymer segments can be selected to degrade over a time period from seven days to 2 years, more preferably from several days to 56 weeks, more preferably from four weeks to 56 weeks, most preferably from eight weeks to 28 weeks.

The branch point can be, for example, an organic molecule which contains three or more functional groups. Preferably, the branch point will contain at least two different types of functional groups (e.g., one or more alcohols and one or more carboxylic acids, or one or more halides and one or more carboxylic acids or one or more amines). In such cases, the different functional groups present on the branch point can be independently addressed synthetically, permitting the covalent attachment of the hydrophobic and hydrophilic segments to the branch point in controlled stoichiometric ratios. In certain embodiments, the branch point is polycarboxylic acid, such as citric acid, tartaric acid, mucic acid, gluconic acid, or 5-hydroxybenzene-1,2,3,-tricarboxylic acid.

In some embodiments, the branch point connects a single hydrophobic polymer segment to three hydrophilic polyethylene glycol polymer segments. In certain cases, the polymer-drug conjugate can be represented by Formula I

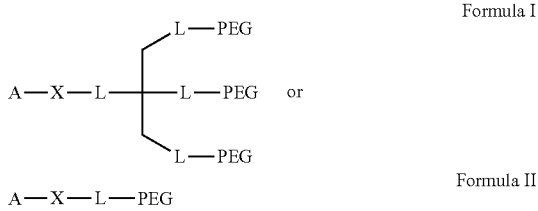

Formula I

Formula II

A—X—L—PEG wherein

A is an active agent, with the proviso that A is not a HIF-1 inhibitor;

L independently for each occurrence, is absent or an ether (e.g., —O—), thioether (e.g., —S—), secondary amine (e.g., —NH—), tertiary amine (e.g., —NR—), secondary amide (e.g., —NHCO—; —CONH—), tertiary amide (e.g., —NRCO—; —CONR—), secondary carbamate (e.g., —OCONH—; —NHCOO—), tertiary carbamate (e.g., —OCONR—; —NRCOO—), urea (e.g., —NHCONH—; —NRCONH—; —NHCONR-_, —NRCONR—), sulfinyl group (e.g., —SO—), or sulfonyl group (e.g., —SOO—);

R is, individually for each occurrence, an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

PEG represents a polyethylene glycol chain; and

X represents a hydrophobic polymer segment.

In certain embodiments, the branch point is a citric acid molecule, and the hydrophilic polymer segments are polyethylene glycol. In such cases, the polymer-drug conjugate can be represented by Formula IA

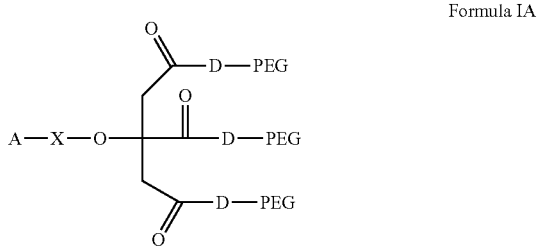

Formula IA wherein

A is an active agent, with the proviso that A is not a HIF-1 inhibitor;

D represents, independently for each occurrence, O or NH;

PEG represents a polyethylene glycol chain; and

X represents a hydrophobic polymer segment.

The non-linear multiblock copolymer-drug conjugates form nanoparticles, microparticles, and implants with improved properties for controlled drug delivery to the eye. Also provided are pharmaceutical compositions containing nano- and/or microparticles formed from one or more polymer-drug conjugates in combination with one or more pharmaceutically acceptable excipients, for example, producing a solution or suspension suitable for injection or topical application to the eye.

Also provided are methods of administering these pharmaceutical compositions, and or an implant containing one or more non-linear multiblock copolymer-drug conjugates, to treat or prevent a diseases or disorders of the eye, such as an intraocular neovascular disease (e.g., wet age-related macular degeneration (AMD), choroidal neovascularization (CNV), and retinal neovascularization (RNV)) or an eye disease associated with inflammation (e.g., uveitis). These formulations and implants can effectively deliver therapeutic levels of one or more active agents to the eye for an extended period of time, in some cases with decreased side effects when compared to administration of the active agent alone.

BRIEF DESCRIPTION OF THE DRAWINGS

FIG. 1A plots the area of CNV (in $mm^2$) observed in the eyes of C57BL/6 mice 14 days after rupture of their Bruch's membrane by laser photocoagulation without administration of an anthracycline (vehicle only injected in both eyes of the mouse (BE), left bar), and upon administration of 10, 1.0, and 0.1 µg of daunorubicin (DNR). Eyes injected with 10 µg of DNR showed a statistically significant reduction in the area of CNV ($P<0.001$, n=10) compared to fellow eyes injected with the vehicle only. Eyes injected with 1.0 µg and 0.1 µg of DNR did not show a statistically significant reduction in the area of CNV (for 1.0 µg, $P<0.082$, n=10; for 0.1 µg, $P<0.399$, n=10) compared to fellow eyes injected with the vehicle only. FIG. 1B plots the area of CNV (in $mm^2$) observed in the eyes of C57BL/6 mice 14 days after rupture of their Bruch's membrane by laser photocoagulation without administration of an anthracycline (vehicle only injected in both eyes of the mouse (BE), left bar), and upon administration of 10, 1.0, and 0.1 µg of doxorubicin (DXR). Eyes injected with 10 µg of DXR showed a statistically significant reduction in the area of CNV ($P<0.001$, n=10) compared to fellow eyes injected with the vehicle only. Eyes injected with 1.0 µg and 0.1 µg of DXR did not show a statistically significant reduction in the area of CNV (for 1.0 µg, $P<0.071$, n=10; for 0.1 µg, $P<0.322$, n=10) compared to fellow eyes injected with the vehicle only. In both FIGS. 2A and 2B, the mean area of CNV was similar in fellow eyes (FE) and eyes from mice in which both eyes were injected with vehicle only (BE), suggesting that there was no systemic effect from intraocular injections of the anthracyclines.

FIG. 2A plots the area of RNV (in mm$^2$) observed in the eyes of C57BL/6 mice with oxygen-induced ischemic retinopathy five days after the administration of a vehicle control (PBS buffer without an anthracycline present, left bar), and upon administration of 1.0, 0.1, and 0.01 µg of daunorubicin (DNR). Eyes injected with 1.0 µg and 0.1 µg of DNR showed a statistically significant reduction in the area of RNV (for 1.0 µg, P<0.001, n=6; for 0.1 µg, P=0.013, n=8). Eyes injected with 0.01 µg of DNR did not show a statistically significant reduction in the area of RNV (P=0.930, n=6). FIG. 2B plots the area of RNV (in mm$^2$) observed in the eyes of C57BL/6 mice with oxygen-induced ischemic retinopathy five days after the administration of a vehicle control (PBS buffer without an anthracycline present, left bar), and upon administration of 1.0, 0.1, and 0.01 µg of doxorubicin (DXR). Eyes injected with 1.0 µg of DXR showed a statistically significant reduction in the area of RNV (P<0.001, n=8). Eyes injected with 0.1 µg and 0.01 µg of DXR did not show a statistically significant reduction in the area of RNV (for 1.0 µg, P=0.199, n=7; for 0.1 µg, P=0.096, n=8).

FIG. 3A is a bar graph plotting the area of CNV (in mm$^2$) observed in the eyes of C57BL/6 mice 14 days after rupture of their Bruch's membrane by laser photocoagulation without administration of an anthracycline (vehicle only injected in both eyes of the mouse (BE), left bar), and upon administration of 10, 1.0, and 0.1 µg of DXR-PSA-PEG$_3$ nanoparticles. In the case of values of CNV measured upon administration of varying amounts of DXR-PSA-PEG$_3$ nanoparticles, the area of CNV observed upon nanoparticle administration is plotted next to the area of CNV observed in untreated fellow eyes (FE). The bars represent the mean (±SEM) area of CNV. Eyes injected with 10 µg, 1.0 µg, and 0.1 µg of DXR-PSA-PEG$_3$ nanoparticles all showed a statistically significant reduction in the area of CNV (for 10 µg, P<0.001, n=10; for 1.0 µg, P=0.009, n=10; for 0.1 µg, P=0.007, n=10) compared to fellow eyes injected with the vehicle only. One cohort had the baseline area of CNV measured, and the remaining mice were treated by injection of 1 µg of DXR-PSA-PEG$_3$ nanoparticles in one eye, and injection of vehicle only in the fellow eye. After an additional seven days, the area of CNV was measured in the DXR-PSA-PEG$_3$ and vehicle-treated eyes.

FIG. 4 is bar graphs plotting the area of RNV (in mm$^2$) observed in the eyes of C57BL/6 mice with oxygen-induced ischemic retinopathy five days after the administration of a vehicle control (PBS buffer without an anthracycline present, right bar), and upon administration of 1 µg of DXR-PSA-PEG$_3$ nanoparticles (left bar). The bars represent the mean (±SEM) area of RNV. A statistically significant decrease in the area of RNV (P<0.001, n=8) was observed relative to fellow eyes injected with vehicle only.

FIG. 5A is a bar graph plotting the area of NV (in mm$^2$) per retina observed four weeks after intraocular injection of 10 µg of DXR-PSA-PEG$_3$ nanoparticles (left bar). A statistically significant decrease in the area of NV per retina (P=0.042, n=5) was observed relative to fellow eyes injected with vehicle only. FIG. 5B is a bar graph plotting the area of NV (in mm$^2$) per retina observed five weeks after intraocular injection of 10 µg of DXR-PSA-PEG$_3$ nanoparticles (left bar). A statistically significant decrease in the area of NV per retina (P=0.007, n=5) was observed relative to fellow eyes injected with vehicle only.

DETAILED DESCRIPTION OF THE INVENTION

I. Definitions

Figure 1A:
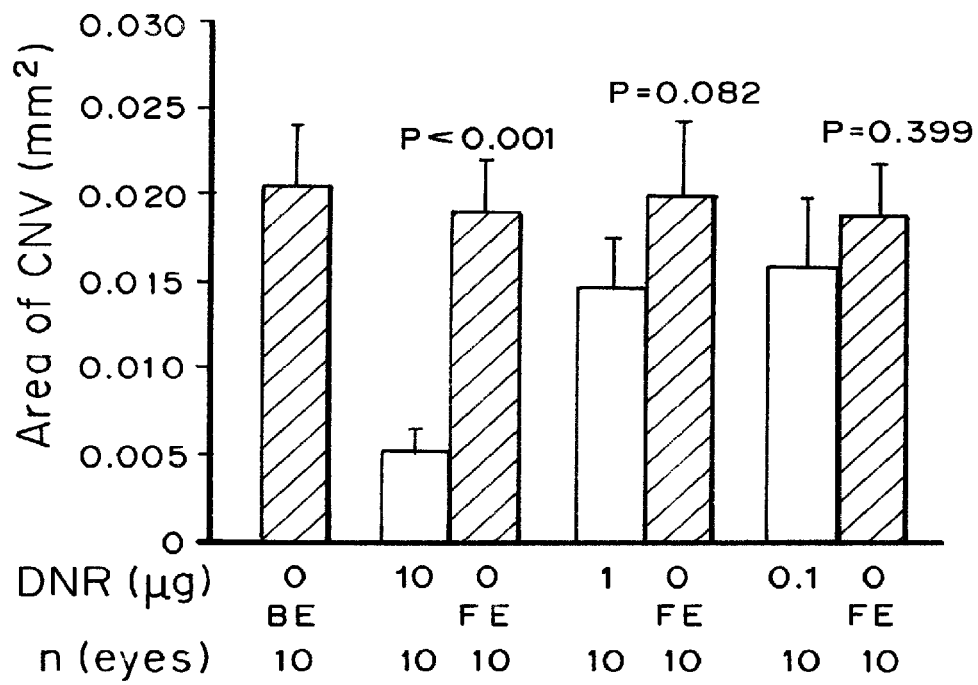
FIGS. 1A-B are bar graphs plotting the area of CNV (in $mm^2$) observed in the eyes of C57BL/6 mice 14 days after rupture of their Bruch's membrane by laser photocoagulation without administration of an anthracycline, and upon administration of varying amounts of doxorubicin or daunorubicin. In the case of values of CNV measured upon anthracycline administration, the area of CNV observed upon anthracycline is plotted next to the area of CNV observed in untreated fellow eyes (FE). The bars represent the mean (±SEM) area of choroidal NV.

"Active Agent", as used herein, refers to a physiologically or pharmacologically active substance that acts locally and/ or systemically in the body. An active agent is a substance that is administered to a patient for the treatment (e.g., therapeutic agent), prevention (e.g., prophylactic agent), or diagnosis (e.g., diagnostic agent) of a disease or disorder. "Ophthalmic Drug" or "Ophthalmic Active Agent", as used herein, refers to a therapeutic or prophylactic agent that is administered to a patient to alleviate, delay onset of, or prevent one or more symptoms of a disease or disorder of the eye, or diagnostic agent useful for imaging or otherwise assessing the eye.

"Effective amount" or "therapeutically effective amount", as used herein, refers to an amount of polymer-drug conjugate effective to alleviate, delay onset of, or prevent one or more symptoms of a disease or disorder being treated by the active agent, and/or an amount of polymer-drug conjugate effective to produce a desired diagnostic signal. In the case of age-related macular degeneration, the effective amount of the polymer-drug conjugate delays, reduces, or prevents vision loss in a patient.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer" as used herein, generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

Hydrophilicity and hydrophobicity can be spoken of in relative terms, such as but not limited to a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

"Nanoparticle", as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle", as used herein, generally refers to a particle having a diameter, such as an average diameter, from about 1 micron to about 100 microns, preferably from about 1 to about 50 microns, more preferably from about 1 to about 30 microns, most preferably from about 1 micron to about 10 microns. The microparticles can have any shape. Microparticles having a spherical shape are generally referred to as "microspheres".

"Molecular weight" as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% or more of the distribution lies within 15% of the median particle size, more preferably within 10% of the median particle size, most preferably within 5% of the median particle size.

"Pharmaceutically Acceptable", as used herein, refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Branch point", as used herein, refers to a portion of a polymer-drug conjugate that serves to connect one or more hydrophilic polymer segments to one or more hydrophobic polymer segments.

"Implant," as generally used herein, refers to a polymeric device or element that is structured, sized, or otherwise configured to be implanted, preferably by injection or surgical implantation, in a specific region of the body so as to provide therapeutic benefit by releasing one or more HIF-1 inhibitors over an extended period of time at the site of implantation. For example, intraocular implants are polymeric devices or elements that are structured, sized, or otherwise configured to be placed in the eye, preferably by injection or surgical implantation, and to treat one or more diseases or disorders of the eye by releasing one or more HIF-1 inhibitors over an extended period. Intraocular implants are generally biocompatible with physiological conditions of an eye and do not cause adverse side effects.

Generally, intraocular implants may be placed in an eye without disrupting vision of the eye.

Ranges of values defined herein include all values within the range as well as all sub-ranges within the range. For example, if the range is defined as an integer from 0 to 10, the range encompasses all integers within the range and any and all subranges within the range, e.g., 1-10, 1-6, 2-8, 3-7, 3-9, etc.

II. Non-Linear Multiblock Copolymer-Drug Conjugates

Non-linear multiblock copolymer-drug conjugates can be used to form nanoparticles, microparticles, and implants (e.g., rods, discs, wafers, etc.) useful for the delivery to the eye. The polymer-drug conjugates contain one or more hydrophobic polymer segments and one or more hydrophilic polymer segments covalently connected through a multivalent branch point to form a non-linear multiblock copolymer containing at least three polymeric segments. The polymer-drug conjugates further contain one or more therapeutic, prophylactic, or diagnostic agents covalently attached to the one or more hydrophobic polymer segments. By employing a polymer-drug conjugate, particles can be formed with more controlled drug loading and drug release profiles. In addition, the solubility of the conjugate can be controlled so as to minimize soluble drug concentration and, therefore, toxicity.

A. Structure of the Non-Linear Multiblock Copolymer-Drug Conjugates

Non-linear multiblock copolymer-drug conjugates are provided which contain an active agent covalently attached to one or more hydrophobic polymer segments which are covalently attached to one or more hydrophilic polymer segments.

The polymer drug conjugates can be represented by the general formula shown below

wherein

A represents, independently for each occurrence, an active agent, with the proviso that A is not a HIF-1 inhibitor;

X represents, independently for each occurrence, a hydrophobic polymer segment;

Y represents a multivalent branch point;

Z represents, independently for each occurrence, a hydrophilic polymer segment m is an integer between one and twenty and n is an integer between zero and twenty.

In some embodiments, m is one or greater and n is zero. In other embodiments, m and n are one or greater, such that m+n is 2 or greater, such, 4, or 5 or greater.

In some embodiments, the conjugate is a mixture of the conjugates above, where, for some conjugates, n is an integer value other than 0 and for other conjugate, n=0.

A can be, independently for each occurrence, an active agent which is useful for the treatment, diagnosis, or prophylaxis of a disease or disorder of the eye (jointly referred to herein as "drug"), with the proviso that A is not a HIF-1 inhibitor.

The one or more hydrophobic polymer segments, independently, can be any biocompatible hydrophobic polymer or copolymer. In some cases, the one or more hydrophobic polymer segments are also biodegradable. Examples of suitable hydrophobic polymers include polyesters such as polylactic acid, polyglycolic acid, or polycaprolactone, polyanhydrides, such as polysebacic anhydride, and copolymers thereof. In certain embodiments, the hydrophobic polymer is a polyanhydride, such as polysebacic anhydride or a copolymer thereof.

The one or more hydrophilic polymer segments can be any hydrophilic, biocompatible, non-toxic polymer or copolymer. The hydrophilic polymer segment can be, for example, a poly(alkylene glycol), a polysaccharide, poly (vinyl alcohol), polypyrrolidone, a polyoxyethylene block copolymer (PLURONIC®) or a copolymers thereof. In preferred embodiments, the one or more hydrophilic polymer segments are, or are composed of, polyethylene glycol (PEG).

In some cases, the polymer-drug conjugate contains only one hydrophilic polymer segment. In preferred embodiments, the polymer-drug conjugate contains more than one hydrophilic polymer chain. In certain embodiments, the polymer-drug conjugate contains between two and six, more preferably between three and five, hydrophilic polymer chains. In one embodiment, the polymer drug conjugate contains three hydrophilic polymer segments.

Preferably, the combined molecular weight of the one or more hydrophilic polymer segments will be larger than the molecular weight of the one or more hydrophobic polymer segments. In some cases, the combined molecular weight of the one or more hydrophilic polymer segments is at least three times, more preferably at least five times, most preferably at least ten times greater than the molecular weight of the one or more hydrophobic polymer segment.

The branch point can be, for example, an organic molecule which contains three or more functional groups. Preferably, the branch point will contain at least two different types of functional groups (e.g., one or more alcohols and one or more carboxylic acids, or one or more halides and one or more carboxylic acids). In such cases, the different functional groups present on the branch point can be independently addressed synthetically, permitting the covalent attachment of the hydrophobic and hydrophilic segments to the branch point in controlled stoichiometric ratios. In certain embodiments, the branch point is polycarboxylic acid, such as citric acid, tartaric acid, mucic acid, gluconic acid, or 5-hydroxybenzene-1,2,3,-tricarboxylic acid.

In certain embodiments, the polymer-drug conjugate is formed from a single hydrophobic polymer segment and two or more hydrophilic polymer segments covalently connected via a multivalent branch point. Exemplary polymer-drug conjugates of this type are represented by the general formula shown below

wherein

A represents an active agent, with the proviso that A is not a HIF-1 inhibitor;

X represents a hydrophobic polymer segment;

Y represents a branch point;

Z represents, independently for each occurrence, a hydrophilic polymer segment; and n is an integer between one or two and 300, more preferably between one or two and fifty, more preferably between one or two and thirty, most preferably between one or two and ten.

In certain embodiments, the polymer-drug conjugate contains between two and six, more preferably between three and five hydrophilic polymer chains. In one embodiment, the polymer drug conjugate contains three hydrophilic polymer segments.

The branch point can be, for example, an organic molecule which contains multiple functional groups. Preferably, the branch point will contain at least two different types of functional groups (e.g., an alcohol and multiple carboxylic acids, or a carboxylic acid and multiple alcohols). In certain embodiments, the branch point is polycarboxylic acid, such as a citric acid molecule.

In some embodiments, the branch point connects a single hydrophobic polymer segment to three hydrophilic polyethylene glycol polymer segments. In certain cases, the polymer-drug conjugate can be represented by Formula I

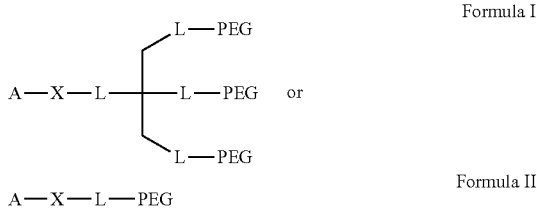

wherein

A is an active agent, with the proviso that A is not a HIF-1 inhibitor;

L independently for each occurrence, is absent or an ether (e.g., —O—), thioether (e.g., —S—), secondary amine (e.g., —NH—), tertiary amine (e.g., —NR—), secondary amide (e.g., —NHCO—; —CONH—), tertiary amide (e.g., —NRCO—; —CONR—), secondary carbamate (e.g., —OCONH—; —NHCOO—), tertiary carbamate (e.g., —OCONR—; —NRCOO—), urea (e.g., —NHCONH—; —NRCONH—; —NHCONR—, —NRCONR—), sulfinyl group (e.g., —SO—), or sulfonyl group (e.g., —SOO—);

R is, individually for each occurrence, an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, CF$_3$, ester, amide, urea, carbamate, thioether, carboxylic acid, and aryl;

PEG represents a polyethylene glycol chain; and

X represents a hydrophobic polymer segment.

In certain embodiments, the branch point is a citric acid molecule, and the hydrophilic polymer segments are polyethylene glycol. In such cases, the polymer-drug conjugate can be represented by Formula IA

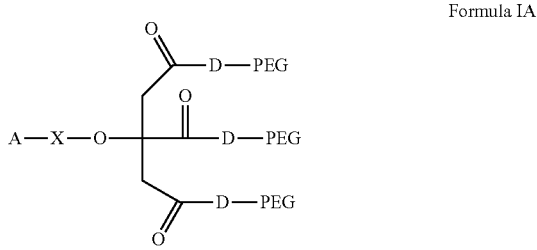

wherein

A is an active agent, with the proviso that A is not a HIF-1 inhibitor;

D represents, independently for each occurrence, O or NH;

PEG represents a polyethylene glycol chain; and

X represents a hydrophobic polymer segment.

In some embodiments, the polymer drug conjugate is defined by the following formula

A-X wherein

A is an active agent, with the proviso that A is not a HIF-1 inhibitor; and

X is a hydrophobic polymer segment, preferably a polyanhydride.

B. Active Agents

Non-linear multiblock copolymer-drug conjugates contain a therapeutic, diagnostic, and/or prophylactic agent. The active agent can be a small molecule active agent and/or a biomolecule, such as an enzyme, protein, growth factor, polypeptide, polysaccharide, lipid, or nucleic acid. Suitable small molecule active agents include organic and organometallic compounds. In some instances, the small molecule active agent has a molecular weight of less than about 2000 g/mol, preferably less than about 1500 g/mol, more preferably less than about 1200 g/mol, most preferably less than about 1000 g/mol. In other embodiments, the small molecule active agent has a molecular weight less than about 500 g/mol. The small molecule active agent can be a hydrophilic, hydrophobic, or amphiphilic compound. Biomolecules typically have a molecular weight of greater than about 2000 g/mol and may be composed of repeat units such as amino acids (peptide, proteins, enzymes, etc.) or nitrogenous base units (nucleic acids).

In preferred embodiments, the active agent is an ophthalmic drug. In particular embodiments, the active agent is a drug used to treat, prevent or diagnose a disease or disorder of the posterior segment eye. Non-limiting examples of ophthalmic drugs include anti-glaucoma agents, anti-angiogenesis agents, anti-infective agents, anti-inflammatory agents, growth factors, immunosuppressant agents, anti-allergic agents, and combinations thereof.

Representative anti-glaucoma agents include prostaglandin analogs (such as travoprost, bimatoprost, and latanoprost), beta-andrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., para-sympathomimetics, such as pilocarpine and ecothiopate), seretonergics muscarinics, dopaminergic agonists, and adrenergic agonists (such as apraclonidine and brimonidine).

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds; MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

In some cases, the active agent is an anti-allergic agent such as olopatadine and epinastine.

Anti-inflammatory agents include both non-steroidal and steroidal anti-inflammatory agents. Suitable steroidal active agents include glucocorticoids, progestins, mineralocorticoids, and corticosteroids.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

In some cases, the active agent is a diagnostic agent imaging or otherwise assessing the eye. Exemplary diagnostic agents include paramagnetic molecules, fluorescent compounds, magnetic molecules, and radionuclides, x-ray imaging agents, and contrast media.

C. Hydrophobic Polymer Segment

The non-linear multiblock copolymer-drug conjugates described herein can contain one or more hydrophobic polymer segments. The one or more hydrophobic polymer segments can be homopolymers or copolymers. Preferably, the one or more hydrophobic polymer segments are biodegradable.

Examples of suitable hydrophobic polymers include polyhydroxyacids such as poly(lactic acid), poly(glycolic acid), and poly(lactic acid-co-glycolic acids); polyhydroxyalkanoates such as poly-3-hydroxybutyrate or poly-4-hydroxybutyrate; polycaprolactones; poly(orthoesters); polyanhydrides; poly(phosphazenes); poly(hydroxyalkanoates); poly (lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In preferred embodiments, the one or more hydrophobic polymer segments are polyanhydrides or copolymers thereof. The polyanhydrides can be aliphatic polyanhydrides, unsaturated polyanhydrides, or aromatic polyanhydrides. Representative polyanhydrides include polyadipic anhydride, polyfumaric anhydride, polysebacic anhydride, polymaleic anhydride, polymalic anhydride, polyphthalic anhydride, polyisophthalic anhydride, polyaspartic anhydride, polyterephthalic anhydride, polyisophthalic anhydride, poly carboxyphenoxypropane anhydride, polycarboxyphenoxyhexane anhydride, as well as copolymers of these polyanhydrides with other polyanhydrides at different mole ratios. Other suitable polyanhydrides are disclosed in U.S. Pat. Nos. 4,757,128, 4,857,311, 4,888,176, and 4,789,724. The one or more hydrophobic polymer segments can also be polyanhydride copolymers, such as a poly(esteranhydrides) or poly(amide-anhydrides). See, for example, U.S. Pat. No. 5,756,652 and U.S. Patent Application No. US 2010/0260703.

In certain embodiments, the hydrophobic polymer segment is polysebacic anhydride. In certain embodiments, the hydrophobic polymer segment is poly(1,6-bis(p-carboxyphenoxy)hexane-co-sebacic acid) (poly(CPH-SA). In certain embodiments, the hydrophobic polymer segment is poly(1,3-bis(p-carboxyphenoxy)propane-co-sebacic acid) (poly(CPP-SA).

In preferred embodiments, the one or more hydrophobic polymer segments are biodegradable. In cases where the one or more hydrophobic polymer segments are biodegradable, the polymer degradation profile may be selected to influence the release rate of the active agent in vivo. For example, the one or more hydrophobic polymer segments can be selected to degrade over a time period from seven days to 24 weeks, more preferably from seven days to eight weeks, preferably from seven days to three weeks. In other cases, the hydrophobic polymer segments can be selected to degrade over a time period from seven days to 2 years, more preferably from seven days to 56 weeks, more preferably from four weeks to 56 weeks, most preferably from eight weeks to 28 weeks.

The molecular weight of the one or more hydrophobic polymer segments can be varied to prepare polymer-drug conjugates that form particles having properties, such as drug release rate, optimal for specific applications. The one or more hydrophobic polymer segments can have a molecular weight of about 150 Da to 1 MDa. In certain embodiments, the hydrophobic polymer segment has a molecular weight of between about 1 kDa and about 100 kDa, more preferably between about 1 kDa and about 50 kDa, most preferably between about 1 kDa and about 25 kDa.

In some cases, the one or more hydrophobic polymer segments have a combined average molecular weight that is less than the combined average molecular weight of the one or more hydrophilic polymer segments of the polymer-drug conjugate. In a preferred embodiment, the one or more hydrophobic polymer segments each have an average molecular weight of less than about 5 kDa.

D. Hydrophilic Polymers

The non-linear multiblock copolymer-drug conjugates described herein also contain one or more hydrophilic polymer segments. Preferably, the polymer-drug conjugates contain more than one hydrophilic polymer segment. In some embodiments, the polymer-drug conjugate contains between two and six, more preferably between three and five, hydrophilic polymer segments. In certain embodiments, the polymer drug conjugate contains three hydrophilic polymer segment.

Each hydrophilic polymer segment can independently contain any hydrophilic, biocompatible (i.e., it does not induce a significant inflammatory or immune response), non-toxic polymer or copolymer. Examples of suitable polymers include, but are not limited to, poly(alkylene glycols) such as polyethylene glycol (PEG), poly(propylene glycol) (PPG), and copolymers of ethylene glycol and propylene glycol, poly(oxyethylated polyol), poly(olefinic alcohol), polyvinylpyrrolidone), poly(hydroxyalkylmethacrylamide), poly(hydroxyalkylmethacrylate), poly(saccharides), poly(amino acids), poly(hydroxy acids), poly(vinyl alcohol), and copolymers, terpolymers, and mixtures thereof.

In preferred embodiments, the one or more hydrophilic polymer segments contain a poly(alkylene glycol) chain. The poly(alkylene glycol) chains may contain between 1 and 500 repeat units, more preferably between 40 and 500 repeat units. Suitable poly(alkylene glycols) include polyethylene glycol, polypropylene 1,2-glycol, poly(propylene oxide), polypropylene 1,3-glycol, and copolymers thereof.

In some embodiments, the one or more hydrophilic polymer segments are copolymers containing one or more blocks of polyethylene oxide (PEO) along with one or more blocks composed of other biocompatible polymers (for example, poly(lactide), poly(glycolide), poly(lactide-co-glycolide), or polycaprolactone). The one or more hydrophilic polymer segments can be copolymers containing one or more blocks of PEO along with one or more blocks containing polypropylene oxide (PPO). Specific examples include triblock copolymers of PEO—PPO-PEO, such as POLOXAMERS™ and PLURONICS™.

In preferred embodiments, the one or more hydrophilic polymer segments are PEG chains. In such cases, the PEG chains can be linear or branched, such as those described in U.S. Pat. No. 5,932,462. In certain embodiments, the PEG chains are linear.

Each of the one or more hydrophilic polymer segments can independently have a molecular weight of about 300 Da to 1 MDa. The hydrophilic polymer segment may have a molecular weight ranging between any of the molecular weights listed above. In certain embodiments, each of the one or more hydrophilic polymer segments has a molecular weight of between about 1 kDa and about 20 kDa, more preferably between about 1 kDa and about 15 kDa, most preferably between about 1 kDa and about 10 kDa. In a preferred embodiment, each of the one or more hydrophilic polymer segments has a molecular weight of about 5 kDa.

E. Branch Points

The non-linear multiblock copolymer-drug conjugates described herein contain a branch point which connects the one or more hydrophilic polymer segments and the one or more hydrophobic polymer segments. The branch point can be any organic, inorganic, or organometallic moiety which is polyvalent, so as to provide more than two points of attachment. In preferred embodiments, the branch point is an organic molecule which contains multiple functional groups.

The functional groups may be any atom or group of atoms that contains at least one atom that is neither carbon nor hydrogen, with the proviso that the groups must be capable of reacting with the hydrophobic and hydrophilic polymer segments. Suitable functional groups include halogens (bromine, chlorine, and iodine); oxygen-containing functional groups such as a hydroxyls, epoxides, carbonyls, aldehydes, ester, carboxyls, and acid chlorides; nitrogen-containing functional groups such as amines and azides; and sulfur-containing groups such as thiols. The functional group may also be a hydrocarbon moiety which contains one or more non-aromatic pi-bonds, such as an alkyne, alkene, or diene. Preferably, the branch point will contain at least two different types of functional groups (e.g., one or more alcohols and one or more carboxylic acids, or one or more halides and one or more alcohols). In such cases, the different functional groups present on the branch point can be independently addressed synthetically, permitting the covalent attachment of the hydrophobic and hydrophilic segments to the branch point in controlled stoichiometric ratios.

Following reaction of the hydrophobic and hydrophilic polymer segments with functional groups on the branch point, the one or more hydrophobic polymer segments and the one or more hydrophilic polymer segments will be covalently joined to the branch point via linking moieties. The identity of the linking moieties will be determined by the identity of the functional group and the reactive locus of the hydrophobic and hydrophilic polymer segments (as these elements react to form the linking moiety or a precursor of the linking moiety). Examples of suitable linking moieties that connect a the polymer segments to the branch point include secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, —NRCONR—), carbinols (—CHOH—, —CROH—), ethers (—O—), and esters (—COO—, —CH$_2$O$_2$C—, CHRO$_2$C—), wherein R is an alkyl group, an aryl group, or a heterocyclic group. In certain embodiments, the polymer segments are connected to the branch point via an ester (—COO—, —CH$_2$O$_2$C—, CHRO$_2$C—), a secondary amide (—CONH—), or a tertiary amide (—CONR—), wherein R is an alkyl group, an aryl group, or a heterocyclic group.

In certain embodiments, the branch point is polycarboxylic acid, such as citric acid, tartaric acid, mucic acid, gluconic acid, or 5-hydroxybenzene-1,2,3,-tricarboxylic acid. Exemplary branch points include the following organic compounds:

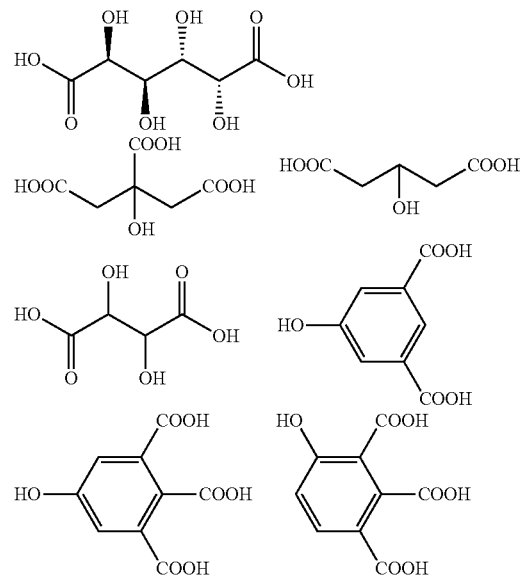

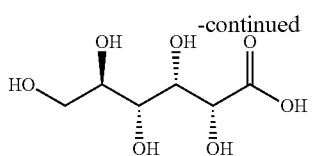

F. Synthesis of Non-Linear Multiblock Copolymer-Drug Conjugates

Non-linear multiblock copolymer-drug conjugates can be prepared using synthetic methods known in the art. Representative methodologies for the preparation of polymer-drug conjugates are discussed below. The appropriate route for synthesis of a given polymer-drug conjugate can be determined in view of a number of factors, such as the structure of the polymer-drug conjugate, the identity of the polymers which make up the conjugate, the identity of the active agent, as well as the structure of the compound as a whole as it relates to compatibility of functional groups, protecting group strategies, and the presence of labile bonds.

In addition to the synthetic methodologies discussed below, alternative reactions and strategies useful for the preparation of the polymer-dug conjugates disclosed herein are known in the art. See, for example, March, "Advanced Organic Chemistry," 5$^{th}$ Edition, 2001, Wiley-Interscience Publication, New York).

Generally, non-linear multiblock copolymer-drug conjugates are prepared by first sequentially attaching the one or more hydrophobic polymer segments and the one or more hydrophilic polymer segments to a branch point to form the polymeric portion of the polymer-drug conjugate. Following assembly of the polymeric components of the polymer-drug conjugate, one or more active agents can then be covalently attached to the one or more hydrophobic polymer segments.

For example, Schemes 1 and 2 illustrate the synthesis of a polymer-drug conjugate (DXR-PSA-PEG$_3$) containing a citric acid branch point functionalized with three hydrophilic PEG segments and a single hydrophobic poly(sebacic anhydride) polymer segment. Doxorubicin (DXR) is bound to the hydrophobic polymer segment.

As shown in scheme 1, citric acid is first reacted with CH$_3$O-PEG-NH$_2$ in the presence of N,N-dicyclohexylcarbodiimide (DCC) and a catalytic amount of 4-dimethylaminopyridine (DMAP), forming amide linkages between the PEG chains and the three carboxylic acid residues of the citric acid branch point. The resulting compound is then reacted with an acylated polysebacic acid precursor (PreSA), and polymerized under anhydrous hot-melt polymerization conditions. As shown in Scheme 2, the resulting polymer (PSA-PEG$_3$) is then reacted with doxorubicin to form the polymer-drug conjugate (DXR-PSA-PEG$_3$).

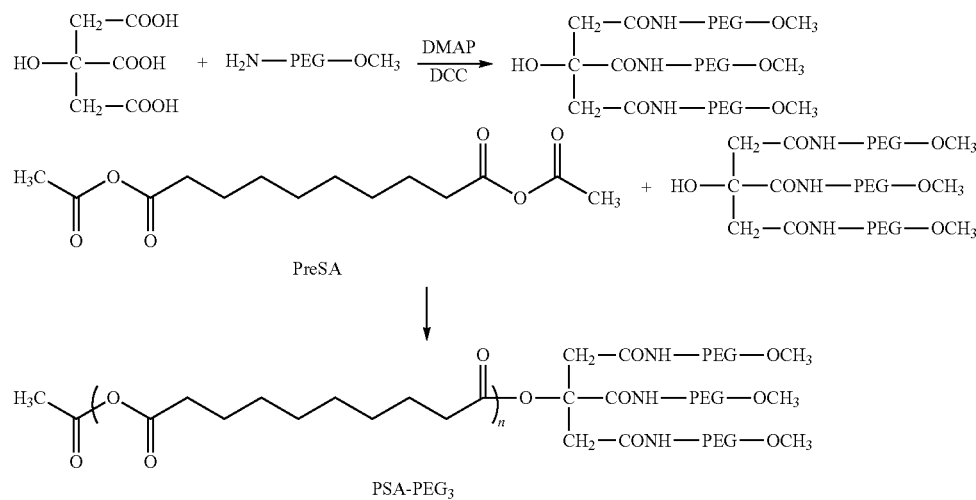

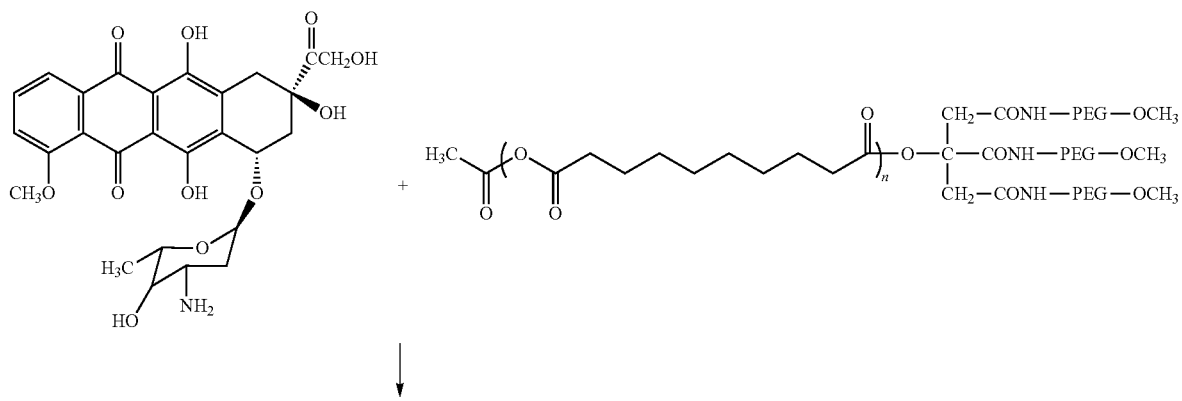

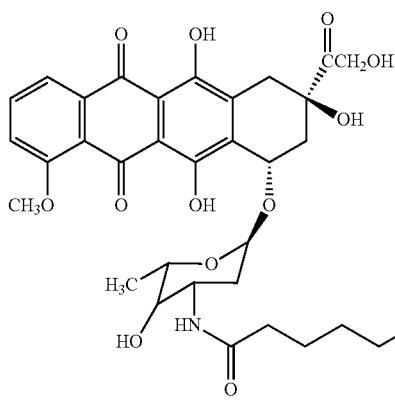
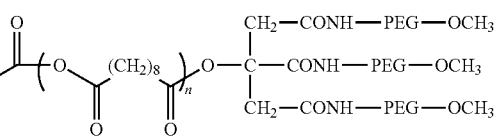

III. Particles and Implants Formed from Polymer-Drug Conjugates

Non-linear multiblock copolymer-drug conjugates can be formed into microparticles, nanoparticles, and implants using a variety of techniques known in the art. An appropriate method for particle or implant formation can be selected in view of the physical and chemical properties of the one or more polymer-drug conjugates used to form the particles/implants (i.e., stability and solubility) as well as the desired particle/implant size and morphology.

A. Particle Morphology

Microparticles and nanoparticles can be formed from one or more polymer-drug conjugates. In some cases, particles are formed from a single polymer-drug conjugate (i.e., the particles are formed from a polymer-drug conjugate which contains the same active agent, hydrophobic polymer segment or segments, branch point (when present), and hydrophilic polymer segment or segments).

In other embodiments, the particles are formed from a mixture of two or more different polymer-drug conjugates. For example, particles may be formed from two or more polymer-drug conjugates containing different active agents and the same hydrophobic polymer segment or segments, branch point (when present), and hydrophilic polymer segment or segments. Such particles can be used, for example, to co-administer two or more active agents. In other cases, the particles are formed from two or more polymer-drug conjugates containing the same active agent, and different hydrophobic polymer segments, branch points (when present), and/or hydrophilic polymer segments. Such particles can be used, for example, to vary the release rate of active agents over time. The particles can also be formed from two or more polymer-drug conjugates containing different active agents and different hydrophobic polymer segments, branch points (when present), and/or hydrophilic polymer segments.

Particles can also be formed from blends of polymer-drug conjugates with one or more additional polymers. In these cases, the one or more additional polymers can be any of the non-biodegradable or biodegradable polymers described in Section C below, although biodegradable polymers are preferred. In these embodiments, the identity and quantity of the one or more additional polymers can be selected, for example, to influence particle stability, i.e. that time required for distribution to the site where delivery is desired, and the time desired for delivery.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. In certain embodiments, the particles are nanoparticles having a diameter of between 500 and 700 nm. The particles can have any shape but are generally spherical in shape.

In some embodiments, the population of particles formed from one or more polymer-drug conjugates is a monodisperse population of particles. In other embodiments, the population of particles formed from one or more polymer-drug conjugates is a polydisperse population of particles. In some instances where the population of particles formed from one or more polymer-drug conjugates is polydisperse population of particles, greater that 50%, 60%, 65%, 70%, 75%, 80%, 85%, 90%, or 95% of the particle size distribution lies within 10% of the median particle size.

Preferably, particles formed from one or more polymer-drug conjugates contain significant amounts of a hydrophilic polymer, such as PEG, on their surface.

B. Methods of Forming Microparticles and Nanoparticles

Microparticle and nanoparticles formed from polymer-drug conjugates can be prepared using any suitable method for the formation of polymer micro- or nanoparticles known in the art. The method employed for particle formation will depend on a variety of factors, including the characteristics of the polymers present in the polymer-drug conjugate and the desired particle size and size distribution. The type of active agent(s) present in the particle-drug conjugate may also be a factor as some agents are unstable in the presence of certain solvents, in certain temperature ranges, and/or in certain pH ranges.

In circumstances where a monodisperse population of particles is desired, the particles may be formed using a method which produces a monodisperse population of nanoparticles. Alternatively, methods producing polydisperse nanoparticle distributions can be used, and the particles can beseparated following particle formation to provide a population of particles having the desired average particle size and particle size distribution. Such separations can be performed using methods known in the art, such as sieving.

Common techniques for preparing microparticles and nanoparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

1. Solvent Evaporation

In this method, the polymer-drug conjugate is dissolved in a volatile organic solvent, such as methylene chloride. The organic solution containing the polymer-drug conjugate is then suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

Polymer-drug conjugates which contain labile polymers, such as certain polyanhydrides, may degrade during the fabrication process due to the presence of water. For these polymers, the following two methods, which are performed in completely anhydrous organic solvents, can be used.

2. Hot Melt Particle Formation

In this method, the polymer-drug conjugate is first melted, and then suspended in a non-miscible solvent (like silicon oil), and, with continuous stirring, heated to 5° C. above the melting point of the polymer-drug conjugate. Once the emulsion is stabilized, it is cooled until the polymer-drug conjugate particles solidify. The resulting nanoparticles are washed by decantation with a suitable solvent, such as petroleum ether, to give a free-flowing powder. The external surfaces of particles prepared with this technique are usually smooth and dense. Hot melt particle formation can be used to prepare particles containing polymer-drug conjugates which are hydrolytically unstable, such as certain polyanhydrides. Preferably, the polymer-drug conjugate used to prepare microparticles via this method will have an overall molecular weight of less than 75,000 Daltons.

3. Solvent Removal

Solvent removal can also be used to prepare particles from polymer-drug conjugates that are hydrolytically unstable. In this method, the polymer-drug conjugate is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the polymer-drug conjugate.

4. Spray Drying

In this method, the polymer-drug conjugate is dissolved in an organic solvent such as methylene chloride. The solution is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

5. Phase Inversion

Particles can be formed from polymer-drug conjugates using a phase inversion method. In this method, the polymer-drug conjugate is dissolved in a "good" solvent, and the solution is poured into a strong non solvent for the polymer-drug conjugate to spontaneously produce, under favorable conditions, microparticles or nanoparticles. The method can be used to produce nanoparticles in a wide range of sizes, including, for example, about 100 nanometers to about 10 microns, typically possessing a narrow particle size distribution.

6. Coacervation

Techniques for particle formation using coacervation are known in the art, for example, in GB-B-929 406; GB-B-929 40 1; and U.S. Pat. Nos. 3,266,987, 4,794,000, and 4,460,563. Coacervation involves the separation of a polymer-drug conjugate solution into two immiscible liquid phases. One phase is a dense coacervate phase, which contains a high concentration of the polymer-drug conjugate, while the second phase contains a low concentration of the polymer-drug conjugate. Within the dense coacervate phase, the polymer-drug conjugate forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

7. Low Temperature Casting

Methods for very low temperature casting of controlled release microspheres are described in U.S. Pat. No. 5,019,400 to Gombotz et al. In this method, the polymer-drug conjugate is dissolved in a solvent. The mixture is then atomized into a vessel containing a liquid non-solvent at a temperature below the freezing point of the polymer-drug conjugate solution which freezes the polymer-drug conjugate droplets. As the droplets and non-solvent for the polymer-drug conjugate are warmed, the solvent in the droplets thaws and is extracted into the non-solvent, hardening the microspheres.

C. Implants Formed from Polymer-Drug Conjugates

Implants can be formed from one or more non-linear multiblock copolymer-drug conjugates. In preferred embodiments, the implants are intraocular implants.

In some cases, the implants are formed from a single polymer-drug conjugate (i.e., the implants are formed from a polymer-drug conjugate which contains the same active agent, hydrophobic polymer segment, branch point (when present), and hydrophilic polymer segment or segments).

In other embodiments, the implants are formed from a mixture of two or more different polymer-drug conjugates. For example, implants may be formed from two or more polymer-drug conjugates containing different active agents and the same hydrophobic polymer segment, branch point (when present), and hydrophilic polymer segment or segments. Such implants can be used, for example, to co-administer two or more active agents. In other cases, the implants are formed from two or more polymer-drug conjugates containing the same active agent, and different hydrophobic polymer segments, branch points (when present), and/or hydrophilic polymer segments. Such implants can be used, for example, to vary the release rate of active agents. The implants can also be formed from two or more polymer-drug conjugates containing different active agents and different hydrophobic polymer segments, branch points (when present), and/or hydrophilic polymer segments.

Implants can also be formed from blends of one or more non-linear multiblock copolymer-drug conjugates with one or more additional polymers. In these cases, the one or more additional polymers can be non-biodegradable or biodegradable polymers, although biodegradable polymers are preferred. In these embodiments, the identity and quantity of the one or more additional polymers can be selected, for example, to influence particle stability, i.e. that time required for distribution to the site where delivery is desired, and the time desired for delivery.

Representative synthetic polymers which can be blended with non-linear multiblock copolymer-drug conjugates include poly(hydroxy acids) such as poly(lactic acid), poly(glycolic acid), and poly(lactic acid-co-glycolic acid), poly (lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

Examples of preferred natural polymers include proteins such as albumin and prolamines, for example, zein, and polysaccharides such as alginate, cellulose and polyhydroxyalkanoates, for example, polyhydroxybutyrate. The in vivo stability of the implant can be adjusted during the production by using polymers such as polylactide-co-glycolide copolymerized with polyethylene glycol (PEG).

Examples of preferred non-biodegradable polymers include ethylene vinyl acetate, poly(meth)acrylic acid, polyamides, copolymers and mixtures thereof.

1. Implant Size and Shape

The implants may be of any geometry such as fibers, sheets, films, microspheres, spheres, rods, circular discs, or plaques. Implant size is determined by factors such as toleration for the implant, location of the implant, size limitations in view of the proposed method of implant insertion, ease of handling, etc.

Where sheets or films are employed, the sheets or films will be in the range of at least about 0.5 mm×0.5 mm, usually about 3 to 10 mm×5 to 10 mm with a thickness of about 0.1 to 1.0 mm for ease of handling. Where fibers are employed, the fiber diameter will generally be in the range of about 0.05 to 3 mm and the fiber length will generally be in the range of about 0.5 to 10 mm.

The size and shape of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Intraocular implants may have a size of between about 5 μm and about 2 mm, or between about 10 μm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm. In certain embodiments, the implant is in the form of an extruded filament with a diameter of about 0.5 mm, a length of about 6 mm, and a weight of approximately 1 mg.

Intraocular implants may also be designed to be least somewhat flexible so as to facilitate both insertion of the implant in the eye, such as in the vitreous, and subsequent accommodation of the implant. The total weight of the implant is usually about 250 to 5000 μg, more preferably about 500-1000 μg. In certain embodiments, the intraocular implant has a mass of about 500 μg, 750 μg, or 1000 μg.

2. Methods of Manufacture

Implants can be manufactured using any suitable technique known in the art. Examples of suitable techniques for the preparation of implants include solvent evaporation methods, phase separation methods, interfacial methods, molding methods, injection molding methods, extrusion methods, coextrusion methods, carver press method, die cutting methods, heat compression, and combinations thereof. Suitable methods for the manufacture of implants can be selected in view of many factors including the properties of the polymer/polymer segments present in the implant, the properties of the one or more active agents present in the implant, and the desired shape and size of the implant. Suitable methods for the preparation of implants are described, for example, in U.S. Pat. No. 4,997,652 and U.S. Patent Application Publication No. US 2010/0124565.

In certain cases, extrusion methods may be used to avoid the need for solvents during implant manufacture. When using extrusion methods, the polymer/polymer segments and active agent are chosen so as to be stable at the temperatures required for manufacturing, usually at least about 85 degrees Celsius. However, depending on the nature of the polymeric components and the one or more active agents, extrusion methods can employ temperatures of about 25 degrees Celsius to about 150 degrees Celsius, more preferably about 65 degrees Celsius to about 130 degrees Celsius.

Implants may be coextruded in order to provide a coating covering all or part of the surface of the implant. Such coatings may be erodible or non-erodible, and may be impermeable, semi-permeable, or permeable to the active agents, water, or combinations thereof. Such coatings can be used to further control release of the active agent from the implant.

Compression methods may be used to make the implants. Compression methods frequently yield implants with faster release rates than extrusion methods. Compression methods may employ pressures of about 50-150 psi, more preferably about 70-80 psi, even more preferably about 76 psi, and use temperatures of about 0 degrees Celsius to about 115 degrees Celsius, more preferably about 25 degrees Celsius.

IV. Pharmaceutical Formulations

Pharmaceutical formulations are provided containing particles formed from one or more polymer-drug conjugates in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

In some cases, the pharmaceutical formulation contains only one type of polymer-drug conjugate particles (i.e., the polymer-drug conjugate particles incorporated into the pharmaceutical formulation have the same composition). In other embodiments, the pharmaceutical formulation contains two or more different types of polymer-drug conjugate particles (i.e., the pharmaceutical formulation contains two or more populations of polymer-drug conjugate particles, wherein the populations of polymer-drug conjugate particles have different chemical compositions, different average particle sizes, and/or different particle size distributions).

A. Additional Active Agents

Pharmaceutical compositions can contain one or more additional active agents which are not present in the polymer-drug conjugate. In some cases, one or more additional active agents may be encapsulated in, dispersed in, or otherwise associated with particles formed from one or more polymer-drug conjugates. In certain embodiments, one or more additional active agents may also be dissolved or suspended in the pharmaceutically acceptable carrier.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

B. Excipients

Particles formed from the polymer-drug conjugates will preferably be formulated as a solution or suspension for injection or topical application to the eye. Pharmaceutical formulations for ocular administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known art, such as dispersing agents, wetting agents, and suspending agents.

For other routes of administration, the particles or drug conjugates may be suspended or emulsified in one or more of the same vehicles as used for ocular administration. These can be administered by injection, drop, spray, topical application, or depo, to a mucosal surface such as the eye (ocular), nose (nasal), mouth (buccal), rectum, vagina, orally, or injection into the bloodstream, tissue or skin.

V. Methods of Use

In certain embodiments, pharmaceutical compositions containing particles formed from one or more of the polymer-drug conjugates are used to treat or prevent one or more diseases of the eye. In some embodiments, implants formed from one or more of the polymer-drug conjugates are used to treat or prevent one or more diseases of the eye.

When administered to the eye, the particles and implants release a low dose of one or more active agents over an extended period of time, preferably longer than 3 days, more preferably longer than 7 days, most preferably longer than ten days. In some embodiments, the particles and implants release an effective amount of one or more active agents over a period of seven days to 24 weeks, more preferably from seven days to eight weeks, preferably from seven days to three weeks. In other cases, the particles and implants release an effective amount of one or more active agents over a period of seven days to 2 years, more preferably from seven days to 56 weeks, more preferably from four weeks to 56 weeks, most preferably from eight weeks to 28 weeks.

The structure of the polymer-drug conjugate, particle/implant morphology, dosage of particles, and the amount of polymer-drug conjugate incorporated in the particle/implant can be tailored to administer a therapeutically effective amount of one or more active agents to the eye over an extended period of time while minimizing side effects, such as the reduction of scoptopic ERG b-wave amplitudes and/or retinal degeneration.

A. Ocular Diseases and Disorders to be Treated

Pharmaceutical compositions containing particles formed from one or more of the polymer-drug conjugates provided herein are administered to the eye of a patient in need thereof to treat or prevent one or more diseases or disorders of the eye. Implants formed from one or more of the polymer-drug conjugates can also be administered to the eye of a patient in need thereof to treat or prevent one or more diseases or disorders of the eye.

In some cases, the disease or disorder of the eye affects the posterior segment of the eye. The posterior segment of the eye, as used herein, refers to the back two-thirds of the eye, including the anterior hyaloid membrane and all of the optical structures behind it, such as the vitreous humor, retina, choroid, and optic nerve.

In preferred embodiments, a pharmaceutical composition containing particles formed from one or more of the polymer-drug conjugates provided herein is administered to treat or prevent an intraocular neovascular disease. In certain embodiments, the particles are formed from a polymer-drug conjugate containing an anthracycline, such as daunorubicin or doxorubicin, which inhibits smooth muscle cell proliferation.

Eye diseases, particularly those characterized by ocular neovascularization, represent a significant public health concern. Intraocular neovascular diseases are characterized by unchecked vascular growth in one or more regions of the eye. Unchecked, the vascularization damages and/or obscures one or more structures in the eye, resulting in vision loss. Intraocular neovascular diseases include proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, central retinal vein occlusion (CRVO), corneal neovascularization, and retinal neovascularization (RNV). Intraocular neovascular diseases afflict millions worldwide, in many cases leading to severe vision loss and a decrease in quality of life and productivity.

Other diseases and disorders of the eye, such as uveitis, are also difficult to treat using existing therapies. Uveitis is a general term referring to inflammation of any component of the uveal tract, such as the iris, ciliary body, or choroid. Inflammation of the overlying retina, called retinitis, or of the optic nerve, called optic neuritis, may occur with or without accompanying uveitis.

Ocular complications of uveitis may produce profound and irreversible loss of vision, especially when unrecognized or treated improperly. The most frequent complications of uveitis include retinal detachment, neovascularization of the retina, optic nerve, or iris, and cystoid macular edema. Macular edema (ME) can occur if the swelling, leaking, and background diabetic retinopathy (BDR) occur within the macula, the central 5% of the retina most critical to vision. ME is a common cause of severe visual impairment.

The neovascularization can be caused by a tumor. The tumor may be either a benign or malignant tumor. Exemplary benign tumors include hamartomas and neurofibromas. Exemplary malignant tumors include choroidal melanoma, uveal melanoma or the iris, uveal melanoma of the ciliary body, retinoblastoma, or metastatic disease (e.g., choroidal metastasis).

The neovascularization may be associated with an ocular wound. For example, the wound may the result of a traumatic injury to the globe, such as a corneal laceration or ophthalmic surgery.

The polymer-drug conjugates can be administered to prevent or reduce the risk of proliferative vitreoretinopathy following vitreoretinal surgery, prevent corneal haze following corneal surgery (such as corneal transplantation and eximer laser surgery), prevent closure of a trabeculectomy, or to prevent or substantially slow the recurrence of pterygii.

The polymer-drug conjugates can be administered to treat or prevent an eye disease associated with inflammation. In such cases, the polymer-drug conjugate preferably contains an anti-inflammatory agent. Exemplary inflammatory eye diseases include, but are not limited to, uveitis, endophthalmitis, and ophthalmic trauma or surgery. The eye disease may also be an infectious eye disease, such as HIV retinopathy, toxocariasis, toxoplasmosis, and endophthalmitis.

Pharmaceutical compositions containing particles formed from one or more of the polymer-drug conjugates can also be used to treat or prevent one or more diseases that affect other parts of the eye, such as dry eye, meibomitis, glaucoma, conjunctivitis (e.g., allergic conjunctivitis, vernal conjunctivitis, giant papillary conjunctivitis, atopic keratoconjunctivitis), neovascular glaucoma with iris neovascularization, and iritis.

The compositions and implants are useful for treatment of other disorders, based on the selection of the active agent and the route of administration. Although there are benefits achieved via the ocular route, including extended efficacy and alleviation of inflammation, the conjugates should also provide benefits and modified pharmacokinetics when administered via another route.

B. Methods of Administration

1. Mode of Administration

The polymer-drug conjugates can be administered locally to the eye by intravitreal injection (e.g., front, mid or back vitreal injection), subconjunctival injection, intracameral injection, injection into the anterior chamber via the temporal limbus, intrastromal injection, intracorneal injection, subretinal injection, and intraocular injection. In a preferred embodiment, the pharmaceutical composition is administered by intravitreal injection.

Alternatively, pharmaceutical compositions containing particles formed from one or more polymer-drug conjugates can be administered via eye drops applied to the surface of the cornea.

For other routes of administration, the particles or drug conjugates may be suspended or emulsified in one or more of the same vehicles as used for ocular administration. These can be administered by injection, drop, spray, topical application, or depo, to a mucosal surface such as the eye (ocular), nose (nasal), mouth (buccal), rectum, vagina, orally, or injection into the bloodstream, tissue or skin.

The implants described herein can be administered to the eye using suitable methods for implantation known in the art. In certain embodiments, the implants are injected intravitreally using a needle, such as a 22-gauge needle. Placement of the implant intravitreally may be varied in view of the implant size, implant shape, and the disease or disorder to be treated.

In some embodiments, a pharmaceutical composition containing particles formed from one or more of the polymer-drug conjugates are co-administered with one or more additional active agents. "Co-administration", as used herein, refers to administration of the polymer-drug conjugates and one or more additional active agents within the same dosage form, as well as administration of the polymer-drug conjugates and one or more additional active agents using different dosage forms simultaneously or as essentially the same time. "Essentially at the same time" as used herein generally means within ten minutes, preferably within five minutes, more preferably within two minutes, most preferably within in one minute.

2. Dosage

Preferably, the particles and implants formed from the polymer-drug conjugates will release an effective amount of one or more therapeutic agent over an extended period of time. In preferred embodiments, the particles and implants release an effective amount of one or more active agents over a period of at least two weeks, more preferably over a period of at least four weeks, more preferably over a period of at least six weeks, most preferably over a period of at least eight weeks. In some embodiments, the particles and implants release an effective amount of one or more active agents over a period of three months or longer.

In some cases, a pharmaceutical formulation containing particles formed from one or more polymer-drug conjugates (or an implant formed from one or more polymer-drug conjugates) is administered to a patient in need thereof in a therapeutically effective amount to decrease choroidal neovascularization. In some embodiments, a pharmaceutical formulation containing particles formed from one or more polymer-drug conjugates (or an implant formed from one or more polymer-drug conjugates) is administered to a patient in need thereof in a therapeutically effective amount to decrease the area of CNV, as measured by fluorescein angiography, by at least 15%, more preferably at least 25%, more preferably at least 40%, most preferably at least 50%.

In some cases, a pharmaceutical formulation containing particles formed from one or more polymer-drug conjugates (or an implant formed from one or more polymer-drug conjugates) is administered to a patient in need thereof in a therapeutically effective amount to decrease retinal neovascularization. In some cases, a pharmaceutical formulation (or an implant formed from one or more polymer-drug conjugates) is administered to a patient in need thereof in a therapeutically effective amount to decrease the area of RNV, as measured by fluorescein angiography, by at least 15%, more preferably at least 25%, more preferably at least 40%, most preferably at least 50%.

An effective dosage can be determined by one of skill in the art based on the known therapeutic efficacy of the drug which is attached to the polymer and determining the pharmacokinetics of the conjugate.

3. Therapeutic Efficacy

In the case of age-related macular degeneration, therapeutic efficacy in a patient can be measured by one or more of the following: assessing the mean change in the best corrected visual acuity (BCVA) from baseline to a desired time, assessing the proportion of patients who lose fewer than 15 letters (3 lines) in visual acuity at a desired time as compared to a baseline, assessing the proportion of patients who gain greater than or equal to 15 letters (3 lines) in visual acuity at a desired time as compared to a baseline, assessing the proportion of patients with a visual acuity Snellen equivalent of 20/2000 or worse at a desired time, assessing the National Eye Institute Visual Functioning Questionnaire, and assessing the size of CNV and the amount of leakage of CNV at a desired time using fluorescein angiography.

In certain embodiments, at least 25%, more preferably at least 30%, more preferably at least 35%, most preferably at least 40% of the patients with recent onset CNV who are treated with the formulations described herein improve by three or more lines of vision.

For other diseases or disorders, efficacy is determined based on a remission or reduction in one or more symptoms of the disease or disorder. For example, in the case of using a drug such as rapamycin to limit uncontrolled proliferation of muscle cells following angioplasty, one would start with a dosage comparable to rapamycin without the polymer, the assess efficacy with this dosage with the polymer, with efficacy being correlated with a decrease in restenosis relative to control.

In the case of treatment of tumors, efficacy can be measured as a decrease in the rate of proliferation, decrease in tumor mass, or decrease in metastasis.

The present invention will be further understood by reference to the following non-limiting examples.

Example 1: Preparation of Polyanhydride-Drug Conjugate Particles

Synthesis of Polymers (Polyethylene glycol)$_3$-co-poly(sebacic acid) (PEG$_3$-PSA) was prepared by melt polycondensation. Briefly, sebacic acid was refluxed in acetic anhydride to form a sebacic acid prepolymer (Acyl-SA). Citric-Polyethylene glycol (PEG$_3$) was prepared using methods known in the art (Ben-Shabat, S. et al. *Macromol. Biosci.* 6:1019-1025 (2006)). 2.0 g of CH$_3$O-PEG-NH$_2$, 26 mg of citric acid, 83 mg of dicyclohexylcarbodiimide (DCC), and 4.0 mg of 4-(dimethylamino)pyridine (DMAP) were added to 10 mL of methylene chloride. This mixture was stirred overnight at room temperature, then precipitated, washed with ether, and dried under vacuum to isolate PEG$_3$. Next, Acyl-SA (90% w/w) and PEG$_3$ (10% w/w) were polymerized at 180° C. for 30 minutes. Nitrogen gas was swept into the flask for 30 seconds every 15 minutes.

The reaction was allowed to proceed for 30 min. Polymers were cooled to ambient temperature, dissolved in chloroform, and precipitated into excess petroleum ether. The precipitate was collected by filtration and dried under vacuum to constant weight.

Formation of DXR-PSA-PEG$_3$ Nanoparticles

DXR-PSA-PEG$_3$ nanoparticles were prepared by dissolving PEG$_3$-PSA with DXR at defined ratios in 3 mL dichloromethane and 1 mL DMSO and reacting for 2 hrs at 50° before homogenizing (L4RT, Silverson Machines, East Longmeadow, Mass.) into 100 mL of an aqueous solution containing 1% polyvinyl alcohol (25 kDa, Sigma). Particles were then hardened by allowing chloroform to evaporate at room temperature while stirring for 2 hours. The particles were collected by centrifugation (20,000×g for 20 min at 4° C.), and washed thrice with double distilled water. Particle size was determined by dynamic light scattering using a ZetaSizer Nano ZS (Malvern Instruments, Southborough, Mass.). Size measurements were performed at 25° C. at a scattering angle of 90°.

DXR Release from DXR-PSA-PEG$_3$ Nanoparticles In Vitro

DXR-PSA-PEG$_3$ nanoparticles were suspended in phosphate buffered saline (PBS, pH 7.4) at 2 mg/mL and incubated at 37° C. on a rotating platform (140 RPM). At selected time points, supernatant was collected by centrifugation (13,500×g for 5 min) and particles were resuspended in fresh PBS. DXR content was measured by absorbance at 480 nm.

Results

The DXR-PSA-PEG$_3$ nanoparticles prepared above contained 23.6% DXR (by weight), and had an average particle size of 647 nm. In vitro studies showed that DXR was released from the nanoparticles as a conjugate with sebacic acid in a steady fashion for up to two weeks under sink conditions in PBS at 37° C. with no initial rapid drug release phase (i.e., no "burst effect").

Example 2: Treatment of Choroidal Neovascularization in a Mouse Model of CNV

Materials and Methods

Pathogen-free C57BL/6 mice (Charles River, Wilmington, Mass.) were treated in accordance with the Association for Research in Vision and Ophthalmology Statement for the Use of Animals in Ophthalmic and Vision Research and the guidelines of the Johns Hopkins University Animal Care and Use Committee.

Choroidal NV was induced by laser photocoagulation-induced rupture of Bruch's membrane as previously described (Tobe, T. et al., Am. J. Pathol. 135(5): 1641-1646 (1998)). Briefly, 5-6-week-old female C57BL/6 mice were anesthetized with ketamine hydrochloride (100 mg/kg body weight) and pupils were dilated. Laser photocoagulation (75 μm spot size, 0.1 sec duration, 120 mW) was performed in the 9, 12, and 3 o'clock positions of the posterior pole of each eye with the slit lamp delivery system of an OcuLight GL diode laser (Iridex, Mountain View, Calif.) and a hand-held cover slip as a contact lens to view the retina. Production of a bubble at the time of laser, which indicates rupture of Bruch's membrane, is an important factor in obtaining CNV; therefore, only burns in which a bubble was produced were included in the study.

Immediately after laser-induced rupture of Bruch's membrane, mice were randomized to various treatment groups for intraocular injections. Intravitreal injections were done under a dissecting microscope with a Harvard Pump Microinjection System and pulled glass micropipettes.

At 1, 4, 7, and 14 days after injection, fundus photographs were taken with a Micron III® camera (Phoenix Research Laboratories Inc., Pleasanton, Calif.). After 14 days, the mice were perfused with 1 ml of PBS containing 25 mg/ml of fluorescein-labeled dextran ($2 \times 10^6$ Daltons average molecular weight; Sigma-Aldrich, St. Louis, Mo.) and choroidal flat mounts were examined by fluorescence microscopy. Images were captured with a Nikon Digital Still Camera DXM1200 (Nikon Instruments Inc., New York, N.Y.). Image analysis software (Image-Pro® Plus; Media Cybernetics, Silver Spring, Md.) was used to measure the total area of CNV at each rupture site with the investigator masked with respect to treatment group.

Treatment of Oxygen-Induced Ischemic Retinopathy

C57BL/6 mice placed in 75% oxygen at postnatal day (P) 7 and at P12 were returned to room air and given an intraocular injection of PBS or PBS containing Daunorubicin, Doxorubicin, or DXR-PSA-PEG$_3$ nanoparticles. At P17, the area of retinal NV on the surface of the retina was measured. Briefly, P17 mice were given an intraocular injection of 1 μl of rat anti-mouse platelet endothelial cell adhesion molecule-1 (PECAM-1) antibody (Pharmingen, San Jose, Calif.) and after 12 hours they were euthanized and eyes were fixed in PBS-buffered formalin for 5 hours at room temperature. Retinas were dissected, washed, and incubated with goat-anti rat polyclonal antibody conjugated with Alexa 488 (Invitrogen, Carlsbad, Calif.) at 1:500 dilution at room temperature for 45 minutes and flat mounted. An observer masked with respect to treatment group measured the area of NV per retina by image analysis.

Treatment of VEGF-Induced Retinal Neovascularization

Hemizygous rhodopsin/VEGF transgenic mice that express VEGF in photoreceptors were given an intraocular injection of 1 μl of PBS or PBS containing 10 μg DXR-PSA-PEG$_3$ nanoparticles at P14. At P21, P28, P35, P42 or P49, the mice were anesthetized, perfused with fluorescein-labeled dextran ($2 \times 10^6$ average molecular weight, Sigma-Aldrich), and retinal flat mounts were examined by fluorescence microscopy (Axioskop2 plus; Zeiss, Thornwood, N.Y.) at 400× magnification, which provides a narrow depth of field, so that when neovascularization along the outer edge of the retina is brought into focus, the remainder of the retinal vessels are out of focus, allowing easy delineation and quantification of the neovascularization. Images were digitized with a three-color charge-coupled device video camera (Cool SNAP™-Pro; Media Cybernetics, Silver Spring, Md.) and a frame grabber. Image analysis software (Image-Pro Plus 5.0; Media Cybernetics, Silver Spring, Md.) was set to recognize fluorescently stained neovascularization and used to calculate the total area of neovascularization per retina. The investigator performing image analysis was masked with respect to treatment group.

Recording of Electroretinograms (ERGs)

Adult C57BL/6 mice were given an intraocular injection of 1 μl of PBS or PBS containing of 0.1, 1.0, or 10 μg of Daunorubicin or Doxorubicin, or 1.0 or 10 μg DXR-PSA-PEG$_3$ nanoparticles. Scotopic and photopic ERGs were recorded at one, seven and 14 days after injection using an Espion ERG Diagnosys machine. For scotopic recordings, mice were dark adapted overnight, and for photopic recordings, mice were adapted for 10 min to background white light at an intensity of 30 cd/m$^2$. The mice were anesthetized with an intraperitoneal injection of ketamine hydrochloride (100 mg/kg body weight) and xylazine (5 mg/kg body weight). Pupils were dilated with Midrin P containing of 0.5% tropicamide and 0.5% phenylephrine, hydrochloride (Santen Pharmaceutical Co., Osaka, Japan). The mice were placed on a pad heated to 39° C. and platinum loop electrodes were placed on each cornea after application of Gonioscopic prism solution (Alcon Labs, Fort Worth, Tex.). A reference electrode was placed subcutaneously in the anterior scalp between the eyes and a ground electrode was inserted into the tail. The head of the mouse was held in a standardized position in a ganzfeld bowl illuminator that ensured equal illumination of the eyes. Recordings for both eyes were made simultaneously with electrical impedance balanced. Scotopic ERGs were recorded at 11 intensity levels of white light ranging from −3.00 to 1.40 log cd-s/m2. Six measurements were averaged for each flash intensity. Photopic ERGs were recorded at three intensity levels of white light ranging from 0.60 to 1.40 log cd-s/m2 with a 30 cd/m2 background. Five measurements were averaged for each flash intensity.

Measurement of Outer Nuclear Layer (ONL) Thickness

ONL thickness was measured. Adult C57BL/6 mice were given an intraocular injection of 1 μl of PBS or PBS containing of 0.1, 1.0, or 10 μg of Daunorubicin or Doxorubicin, or 1.0 or 10 μg DXR-PSA-PEG$_3$ nanoparticles. Mice were euthanized, a mark was placed at 12:00 at the corneal limbus, and eyes were removed and embedded in optimal cutting temperature compound. Ten micrometer frozen sections were cut parallel to the 12:00 or 9:00 meridian through the optic nerve and fixed in 4% paraformaldehyde. The sections were stained with hematoxylin and eosin, examined with an Axioskop microscope (Zeiss, Thornwood, N.Y.), and images were digitized using a three charge-coupled device (CCD) color video camera (IK-TU40A; Toshiba, Tokyo, Japan) and a frame grabber. Image-Pro Plus software (Media Cybernetics, Silver Spring, Md.) was used to outline the ONL. With the observer masked with respect to treatment group, ONL thickness was measured at six locations, 25% (S1), 50% (S2), and 75% (S3) of the distance between the superior pole and the optic nerve and 25% (I1), 50% (I2), and 75% (I3) of the distance between the inferior pole the optic nerve.

Statistical Analysis

Data were expressed as mean±SEM. Statistical analysis was performed using Student's t-test and P<0.05 was considered significant.

Results

Anthracyclines Suppress Choroidal and Retinal NV

Figure 1B:
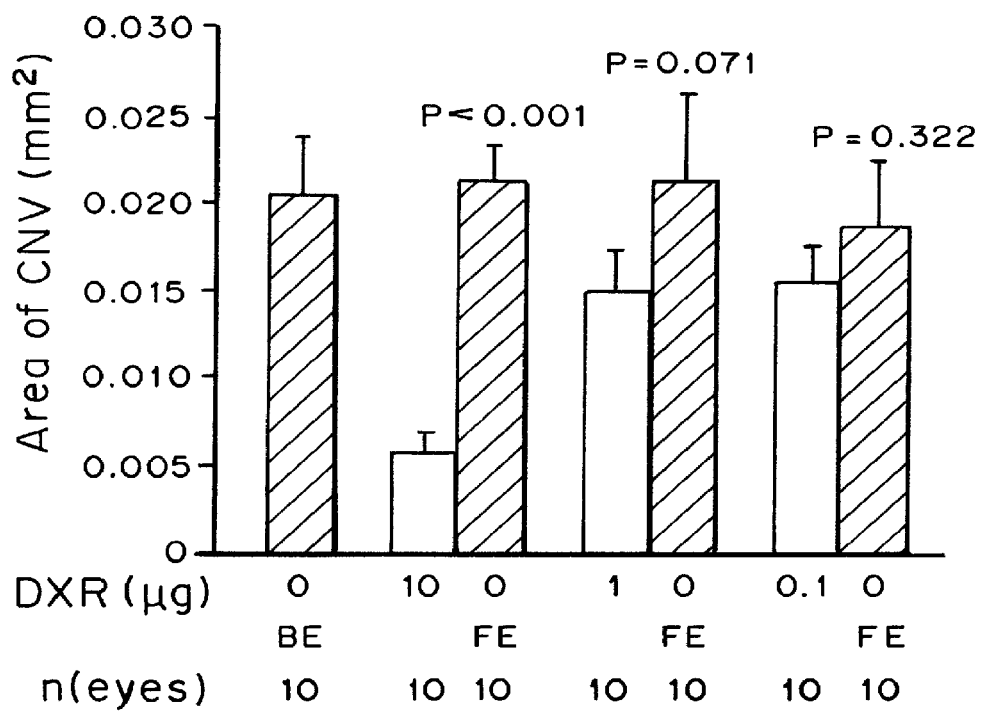

In a mouse model of choroidal NV (Tobe, T. et al. *Am. J. Pathol.* 153:1641-1646 (1998)) that is predictive of drug effects in patients with neovascular AMD (Saishin, Y. et al. *J. Cell Physiol.* 195:241-248 (2003)), intraocular injection of 10 µg of DNR suppressed choroidal NV, while injection of 1 or 0.1 µg had no significant effect (FIG. 1A). Similarly, intraocular injection of 10 µg of DXR suppressed choroidal NV and injections of 1 or 0.1 µg did not have a significant effect (FIG. 1B).

Figure 2A:
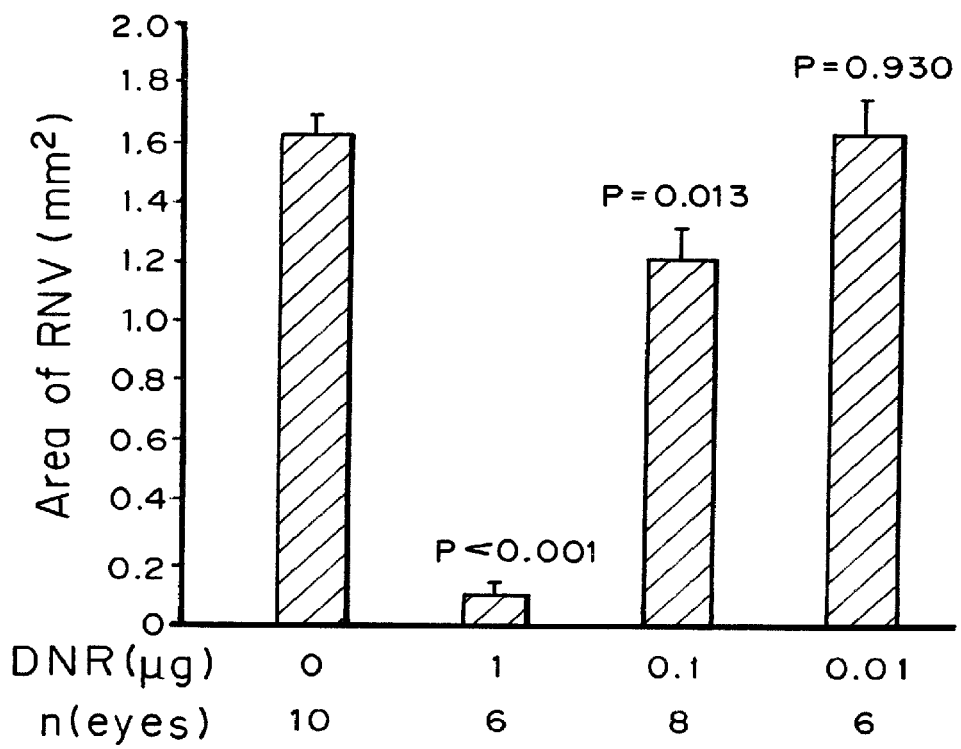
FIGS. 2A-B are bar graphs plotting the area of RNV (in mm$^2$) observed in the eyes of C57BL/6 mice with oxygen-induced ischemic retinopathy five days after the administration of a vehicle control (PBS buffer without an anthracycline present), and upon administration of varying amounts of doxorubicin or daunorubicin. The bars represent the mean (±SEM) area of RNV.
Figure 2B:
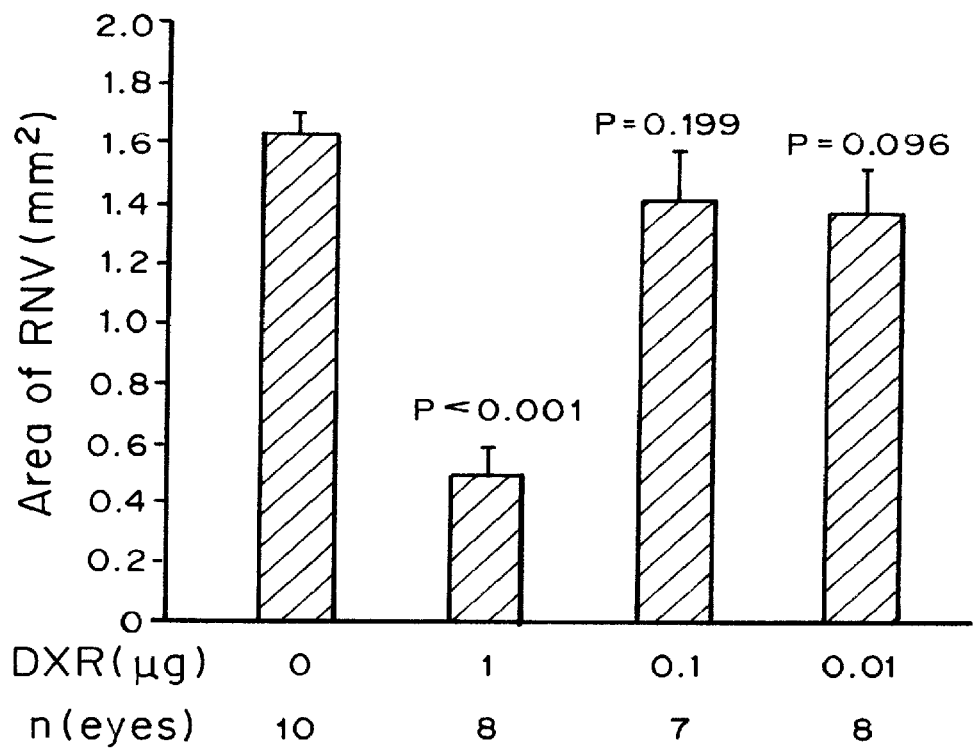

In neonatal mice with oxygen-induced ischemic retinopathy, a model predictive of effects in proliferative diabetic retinopathy, intraocular injection of 1 µg of DNR markedly reduced the area of retinal NV, 0.1 µg caused a small reduction, and 0.01 µg had no significant effect (FIG. 2A). The NV was visualized on retinal flat mounts after in vivo immunofluorescent staining with anti-PECAM1, a technique that selectively stains NV and hyaloid vessels. Intraocular injection of 1 µg of DXR, but not 0.1 or 0.01 µg, significantly reduced the area of retinal NV (FIG. 2B). Five days after injection of 1 µg of DNR or DXR, precipitated drug was visualized on the surface of the retina. The mean area of choroidal or retinal NV in fellow eyes was not significantly different from that in eyes of mice in which both eyes were injected with vehicle indicating that there was no systemic effect from intraocular injections of DNR or DXR.

Effect of Intraocular Injections of DNR or DXR on Retinal Function

Since DNR and DXR are antimetabolites as well as HIF-1 inhibitors we examined their effect on retinal function assessed by ERGs. Fourteen days after intraocular injections of 1 µg, but not 0.1 µg, of DNR or DXR there was a significant reduction in mean scotopic and photopic b-wave amplitudes. These data indicate that while DNR and DXR strongly suppress ocular NV, bolus injections of free drugs can cause retinal toxicity.

Retinal Toxicity after Intraocular Injection of Digoxin

It has been previously demonstrated that intraocular injections of 0.01-0.25 µg of digoxin suppress HIF-1 transcriptional activity and ocular NV (Yoshida, T. et al. *FASEB J.* 24:1759-1767 (2010)). To explore whether the deleterious effects of DXR and DNR on retinal function might be related to their suppression of HIF-1 activity, the effects of intraocular injection of 0.25 and 0.05 µg of digoxin on retinal function were measured. One week after intraocular injection of 0.25 µg of digoxin, there was a significant reduction in mean scotopic a-wave amplitude, mean scotopic b-wave amplitude, and mean photopic b-wave amplitude. There was also a reduction in outer nuclear layer thickness at 3 of 6 measurement locations in the retina, indicating death of photoreceptor cells. These results are consistent with substantial toxicity after intraocular injection of 0.25 µg of digoxin. Intraocular injection of 0.05 µg of digoxin was less toxic, but still caused significant reduction in mean scotopic and photopic b-wave amplitudes. Thus, for both anthracyclines and digoxin, injection of free drug into the eye carries risk of retinal toxicity.

Effect of DXR Polymer Nanoparticles on Ocular NV

The effect of intraocular injection of DXR nanoparticles was first tested in mice with laser-induced choroidal NV. After laser-induced rupture of Bruch's membrane, C57BL/6 mice received an intraocular injection of 10, 1.0, or 0.1 µg of DXR-PSA-PEG$_3$ nanoparticles. Fundus photos of the animals that received 1 µg of DXR-PSA-PEG$_3$ nanoparticles showed a large orange mass of nanoparticles overlying the posterior retina 1 day after injection that decreased slowly over time and was still readily visible on day 14. Particles remained visible over periods of time as long as five weeks.

Figure 3A:
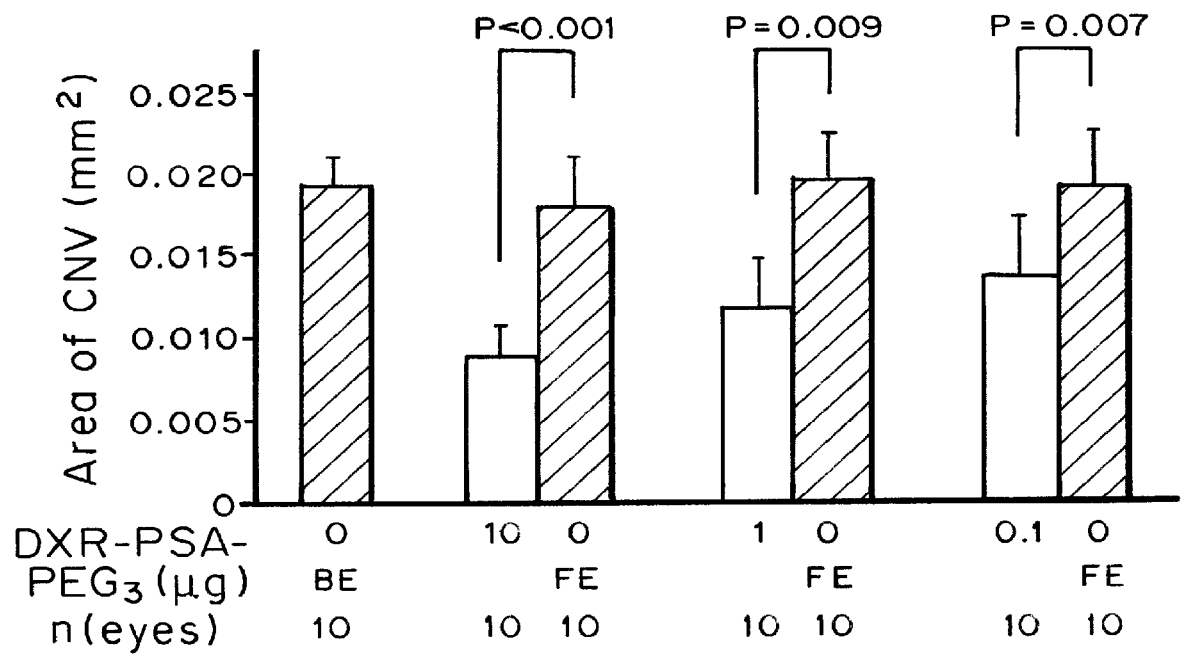
FIG. 3A is a graph demonstrating the efficacy of a non-linear multiblock copolymer-drug conjugate (specifically DXR-PSA-PEG$_3$ nanoparticles) in treating CNV in a mouse model of CNV.

In mice perfused with fluorescein-labeled dextran to visualize choroidal NV by fluorescence microscopy at day 14, the area of choroidal NV appeared smaller in eyes given an intraocular injection of DXR-PSA-PEG$_3$ nanoparticles compared to fellow eyes injected with PBS. Image analysis confirmed that compared to eyes injected with PBS, the mean area of choroidal NV was significantly less in eyes injected with 10, 1, or 0.1 µg of DXR-PSA-PEG$_3$ nanoparticles (FIG. 3A).

Figure 3B:
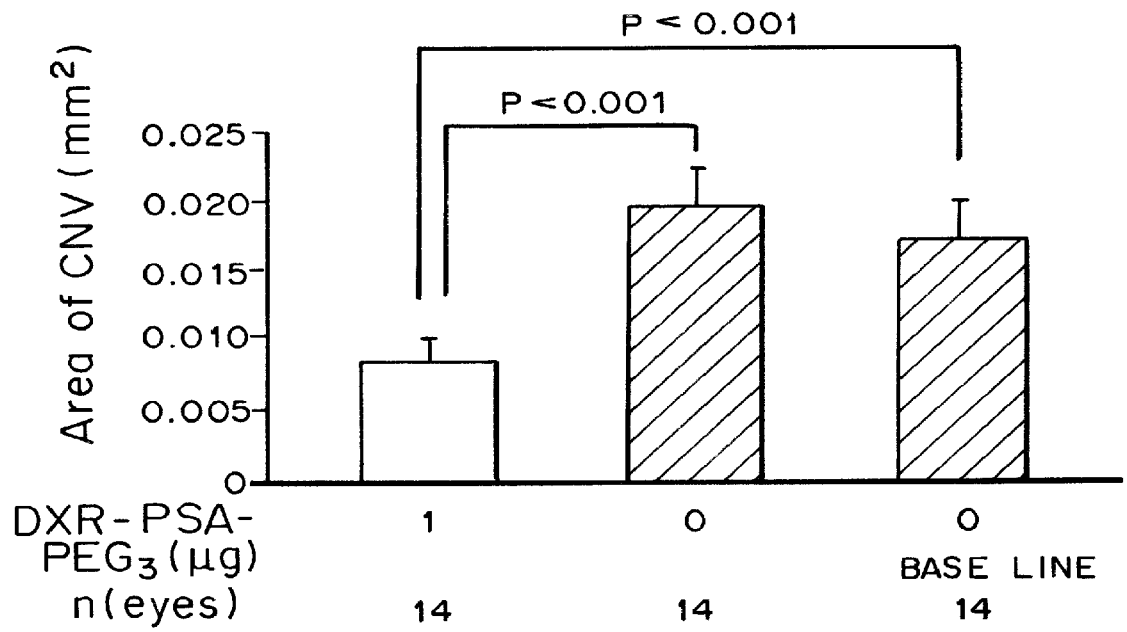
FIG. 3B is a bar graph plotting the area of CNV (in mm$^2$) observed seven days after administration of 1 µg of DXR-PSA-PEG$_3$ nanoparticles (left bar) and 14 days after laser photocoagulation rupture of Bruch's membrane. The area of CNV (in mm$^2$) observed seven days after administration of 1 µg of DXR-PSA-PEG$_3$ nanoparticles and 14 days after laser photocoagulation rupture of Bruch's membrane is compared with the area of CNV measured in fellow eyes injected with vehicle only (center bar) 14 days after laser photocoagulation rupture of Bruch's membrane and seven days after vehicle injection and untreated eyes seven days after laser photocoagulation rupture of Bruch's membrane (Base line; right bar). A statistically significant decrease in the area of CNV (P<0.001, n=10) was observed, both relative to fellow eyes injected with vehicle only (center bar) and the base line CNV observed seven days after laser photocoagulation rupture of Bruch's membrane in untreated eyes (right bar), demonstrating that DXR-PSA-PEG$_3$ treatment not only significantly reduced CNV (compare left and middle bars), but also mediated regression of existing CNV (compare left and right bars).

The effect of DXR-PSA-PEG$_3$ nanoparticles on already established choroidal NV was investigated by allowing the NV to grow for 7 days and then injecting 1 µg of DXR-PSA-PEG$_3$ nanoparticles. Seven days after injection, eyes injected with DXR-PSA-PEG$_3$ nanoparticles had a mean area of choroidal NV that was significantly less than that seen in control eyes injected with PBS, and also significantly less than the baseline amount of choroidal NV that was present at 7 days (FIG. 3B). This indicates that DXR-PSA-PEG$_3$ nanoparticles cause regression of established choroidal NV.

Figure 4:
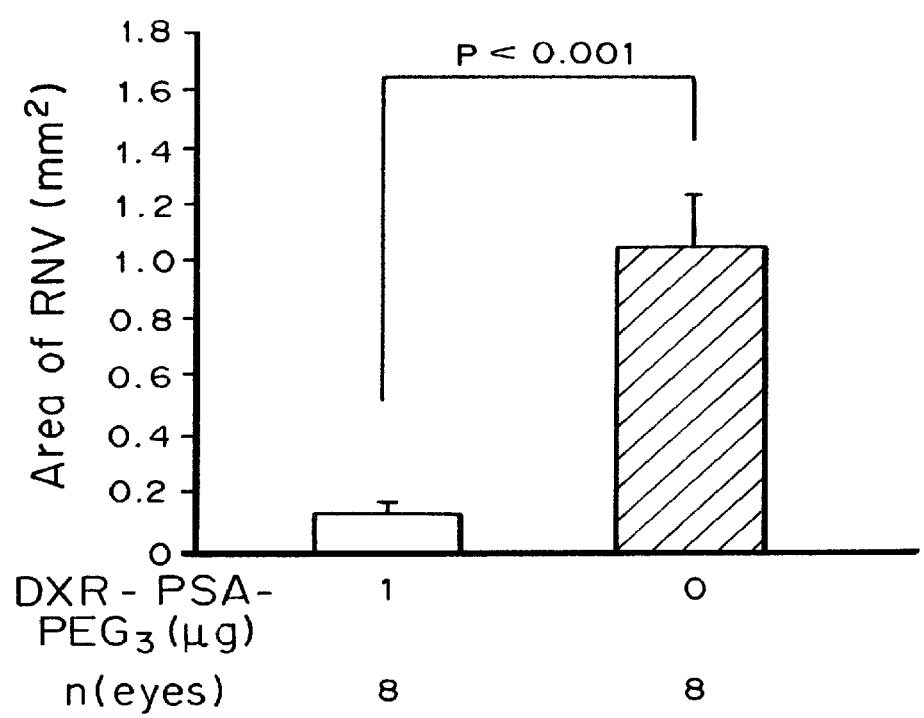
FIG. 4 is a graph demonstrating the efficacy of a non-linear multiblock copolymer-drug conjugate (specifically DXR-PSA-PEG$_3$ nanoparticles) in treating RNV in mice with oxygen-induced ischemic retinopathy.

The DXR-PSA-PEG$_3$ nanoparticle formulation was also investigated using a model of ischemia-induced retinal neovascularization (Smith, L. E. H. et al. *Invest. Ophthalmol. Vis. Sci.* 35:101-111 (1994)). Intraocular injections of 1 µg of DXR-PSA-PEG$_3$ nanoparticles significantly reduced the mean area of retinal NV compared to fellow eyes injected with PBS (FIG. 4).

Prolonged Suppression of NV after Intraocular Injection of DXR Polymer Nanoparticles in Rho/VEGF Transgenic Mice Rho/VEGF transgenic mice, in which the rhodopsin promoter drives expression of VEGF in photoreceptors, have sustained expression of VEGF starting at postnatal day (P) 7, and provide an excellent model to test the duration of activity of a therapeutic agent (Okamoto, N. et. al. *Am. J. Pathol.* 151:281-291 (1997)).

Figure 5A:
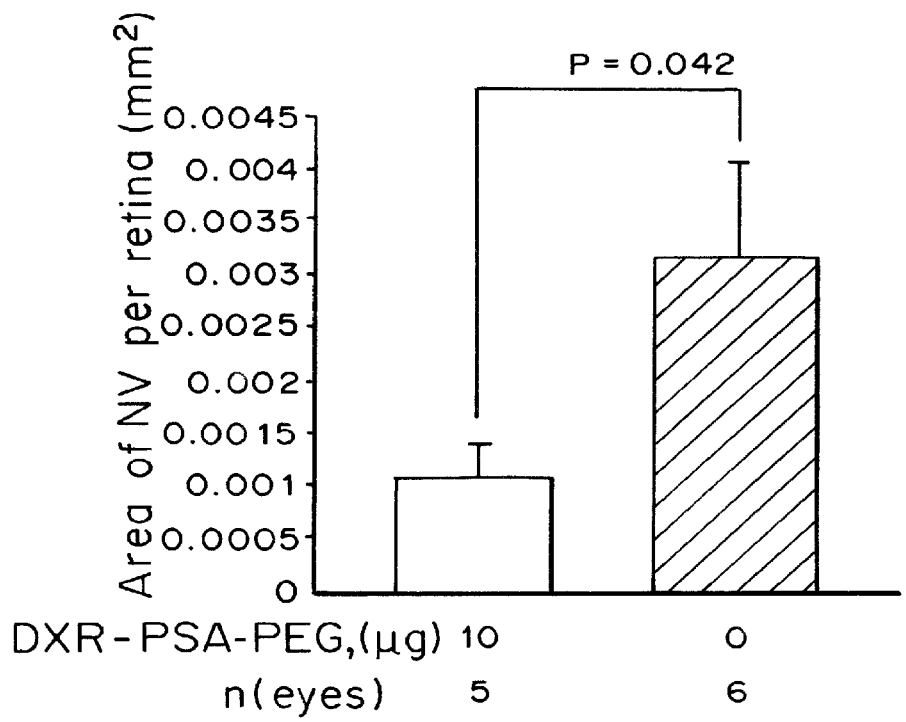
FIGS. 5A-B are bar graphs demonstrating the ability of a non-linear multiblock copolymer-drug conjugate (specifically DXR-PSA-PEG$_3$ nanoparticles) to suppress subretinal neovascularization (NV) in transgenic mice in which the rhodopsin promoter drives expression of VEGF in photoreceptors (rho/VEGF mice) for at least 35 days. At postnatal day (P) 14, hemizygous rho/VEGF mice were given an intraocular injection of 10 µg of DXR-PSA-PEG$_3$ nanoparticles in one eye and vehicle only (PBS buffer) in the fellow eye.
Figure 5B:
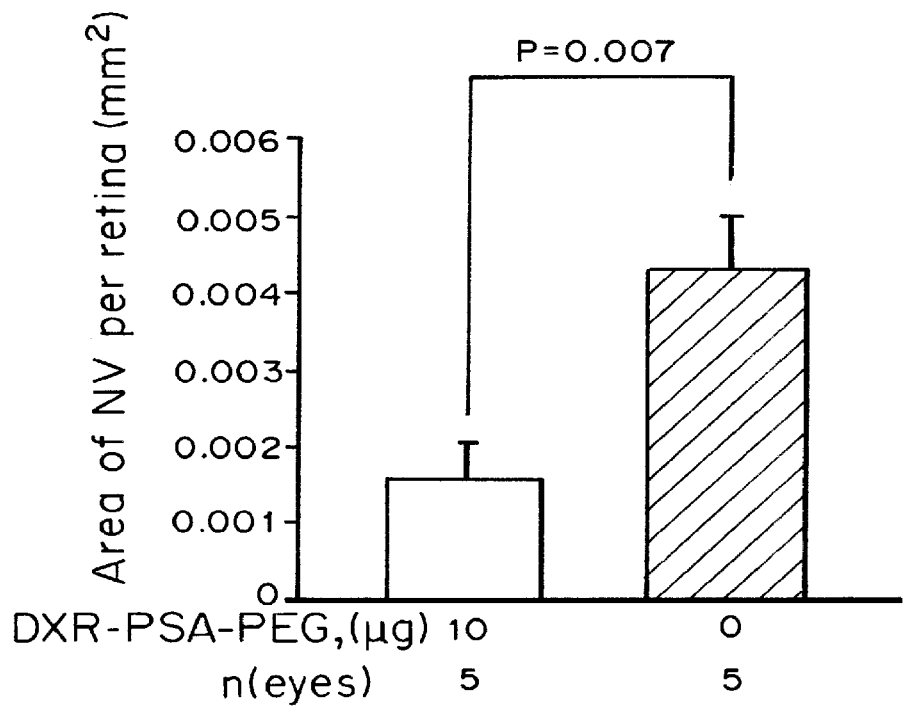

At P14, hemizygous rho/VEGF mice were given an intraocular injection of 10 µg of DXR-PSA-PEG$_3$ nanoparticles in one eye and PBS in the fellow eye. At 4 (FIG. 5A) or 5 weeks (FIG. 5B) after injection the mean area of subretinal NV was significantly less in DXR nanoparticle-injected eyes than vehicle-injected fellow eyes.

Intraocular Injection of 1 or 10 µg of DXR Nanoparticles Did not Cause Toxicity as Measured by ERG or ONL Thickness At 14 days after intraocular injection of 10 µg of DXR-PSA-PEG$_3$, there was no significant difference in scotopic or photopic b-wave amplitudes compared to PBS-injected eyes. There was also no difference in outer nuclear layer thickness indicating that DXR nanoparticles did not cause photoreceptor cell death.

Example 3. Pharmacokinetic Study in Rabbits

Materials and Methods

Preparation of the PEG$_3$-PSA Polymer (Polyethylene glycol)3-co-poly(sebacic acid)(PEG$_3$-PSA) was synthesized by melt condensation. Briefly, sebacic acid was refluxed in acetic anhydride to form sebacic acid prepolymer (Acyl-SA). Polyethylene glycol (PEG$_3$) was prepared by mixing CH$_3$O-PEG-NH$_2$ (2.0 g), citric acid (26 g), dicyclohexylcarbodiimide (DCC; 83 mg) and 4-(dimethylamino)pyridine (DMAP, 4.0 mg) which were added to 10 mL methylene chloride, stirred overnight at room temperature, then precipitated and washed with ether, and dried under vacuum. Next, Acyl-SA (90% w/w) and $PEG_3$ (10% w/w) were polymerized at 180° C. for 30 minutes. Nitrogen gas was swept into the flask for 30 seconds every 15 minutes.

Polymers were cooled to ambient temperature, dissolved in chloroform and precipitated into excess petroleum ether. The precipitate was collected by filtration and dried under vacuum to constant weight, to produce the $PEG_3$-PSA polymer.

Preparation of the DXR-PSA-$PEG_3$ Microparticles and Nanoparticles

To prepare DXR-PSA-$PEG_3$ nanoparticles, 80 mg $PEG_3$-PSA was dissolved in 6 mL dichloromethane (DCM) and 20 mg doxorubicin hydrochloride (DXR) (NetQem LLC, Durham, N.C.) was dissolved in 2 mL dimethylsulfoxide (DMSO). The solutions of polymer and drug were mixed and kept at 50° C. for 30 min. The resulting mixture was homogenized in 50 mL of 1% polyvinyl alcohol (PVA) solution (25 kDa, Polyscience, Niles, Ill.) at 10,000 rpm for 3 min using a L4RT homogenizer (Silverson Machines, East Longmeadow, Mass.). The particle suspension was stirred at room temperature for 2 hours to remove dichloromethane. The particles were collected by centrifugation (20,000×g for 20 minutes at 4° C.) and washed thrice with ultrapure water prior to lyophilization.

DXR-PSA-$PEG_3$ microparticles were prepared in a similar fashion. Briefly, 200 mg $PEG_3$-PSA was dissolved in 3 mL DCM and mixed with 40 mg DXR dissolved in 1.5 mL DMSO. Following incubation at 50° C. for 30 min, the mixture was homogenized in 100 mL of PVA at 3,000 rpm for 1 min. After stirring for 2 hr, particles were collected by centrifugation (9,000×g for 25 minutes) and washed thrice before lyophilization.

Particle Characterization

Particle size was determined using a Coulter Multisizer IV (Beckman-Coulter Inc., Fullerton, Calif.). Greater than 100,000 particles were sized for each batch of microparticles to determine the mean particle diameter. Particle morphology was characterized by scanning electron microscopy (SEM) using a cold cathode field emission SEM (JEOL JSM-6700F, Peabody, Mass.). Drug loading was determined by dissolving dry powder of the particles in DCM and DMSO and the absorbance was measured using a UV spectrophotometer at 490 nm.

Animal Procedures

Pigmented, Dutch-Belted rabbits were used for these studies (n=10). Animals were treated in accordance with the Association for Research in Vision and Ophthalmology Statement of Use of Animals in Ophthalmic and Research and the guidelines of the Johns Hopkins University Animal Care and Use Committee. For intraocular injections and collection of aqueous humor, animals were anesthetized with an intramuscular injection of ketamine (25 mg/kg) and xylazine (2.5 mg/Kg). When sedated, the pupils were dilated with 2.5% phenylephrine hydrochloride and 10% tropicamide. Ocular surface anesthesia was performed using topical instillation of 0.5% proparacaine hydrochloride.

For the injections, a 26-gauge needle was carefully introduced into the vitreous cavity, 1.5 mm posterior to the superotemporal limbus, with the needle tip directed into the mid-vitreous. A volume of 0.1 mL of DXR-PSA-$PEG_3$ micro or nanoparticle suspension was delivered to the right eyes, and 0.1 mL vehicle (PBS) was delivered to the left eyes. The needle was held in place for 10 seconds before withdrawal to prevent reflux from the entry site. Animals were returned to their cages and monitored until anesthesia was reversed.

At the indicated times, aqueous humor was withdrawn (~0.1 mL) by inserting a 30-gauge needle through the limbus and removing the aqueous humor. The samples were stored at −80° C. until use. At the end of the study (Day 105 for the nanoparticle-treated animals and Day 115 for the microparticle-treated animals), animals were euthanized using a pentobarbital-based euthanasia (>150 mg/Kg). Animals were enucleated and vitreous was isolated and stored at −80° C. until use.

HPLC Quantitation of Released Drug Conjugates in Rabbit Aqueous Humor and Vitreous Samples Prior to quantitation of the drug content by HPLC, 100 µL of aqueous humor sample or vitreous sample was mixed with 200 µL of methanol and incubated at 4° C. for 3 hr. After centrifugation (15,000×g, 10 min) and filtration through a 0.2 µm PTFE filter, 150 µL of the filtrate was injected into a Waters HPLC system equipped with a c18 reverse phase column (5 µm, 4.6×250 mm; Grace, Deerfield Ill.). Released drug conjugate was eluted by an isocratic mobile phase containing water and acetonitrile (60%:40%, v/v) at 1 mL/min and detected using a fluorescence detector (excitation wavelength: 500 nm, emission wavelength: 551 nm). The estimated limit of detection was 10 ng/mL or 20 nM. A series of DXR aqueous solutions at different concentrations were used as calibration standards. The data was analyzed using Empower 3 chromatography data software (Waters Corporation, Milford Mass.).

Results

DXR-PSA-$PEG_3$ Microparticles and Nanoparticles

Microparticles and nanoparticles composed of the DXR-SA-$PEG_3$ conjugate were synthesized and characterized as described. Particles were sized prior to lyophilization and following reconstitution in vehicle (PBS). The microparticles displayed a mean size of 27.2+1.0 um, and the nanoparticles, 0.98+0.02 um prior to lyophilization (Table 1; FIG. 6). The average drug loading of the microparticles was 13% and the nanoparticles was 20% (Table 1).

TABLE 1

Characterization of DXR-PSA-$PEG_3$ Micro and Nanoparticles

| Type | Sample ID Prior to lyophilization | Particle Diameter by Volume Post-reconstitution in PBS | Average Drug Loading (w/w) |
|---|---|---|---|
| Microparticles | 27.2 ± 10.4 µm | 24.3 ± 8.3 µm | 13% |
| Nanoparticles | 0.98 ± 0.74 µm | 3.7 ± 2.0 µm | 20% |

Figure 6A:
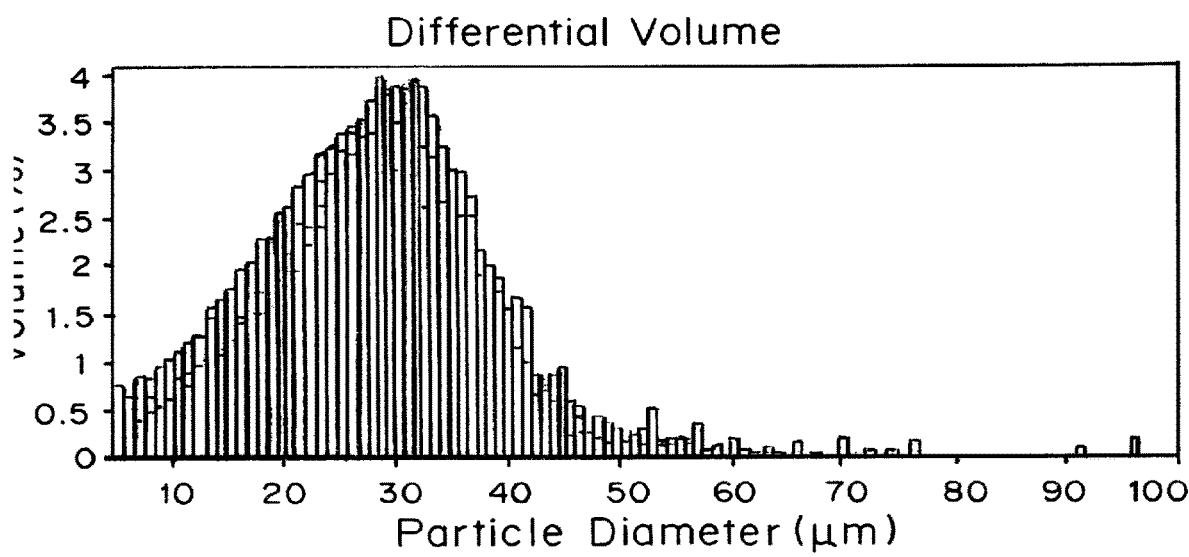
FIG. 6A is a graph showing the size distribution by volume of microparticles as determined using a Coulter Multisizer.
Figure 6B:
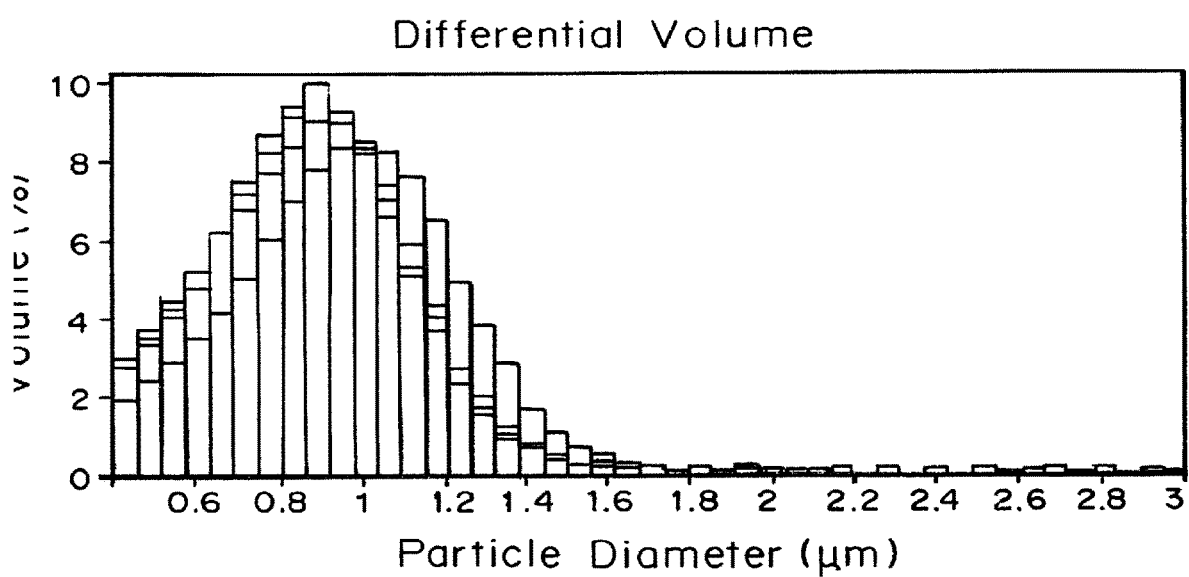
FIG. 6B is a graph showing the size distribution by volume of nanoparticles as determined using a Coulter Multisizer.

SEM analyses demonstrated discrete particles of the expected size. FIGS. 6A and 6B show the size distribution by volume of the microparticles and nanoparticles, respectively.

Duration of Drug Release Following IVT Administration to Rabbits

Rabbits received an intravitreal injection (0.1 mL) of the DXR-PSA-$PEG_3$ microparticles or nanoparticles into their right eyes and vehicle alone (PBS) into their left eyes. At the indicated times, aqueous humor was collected (~0.1 mL) and analyzed for the presence of released drug conjugate using a quantitative HPLC-based assay. On Day 115 (microparticle group) or Day 105 (nanoparticle group), animals were euthanized and aqueous humor and vitreous was collected.

The released drug levels in the AH were compared to that in the vitreous for each animal.

Figure 7A:
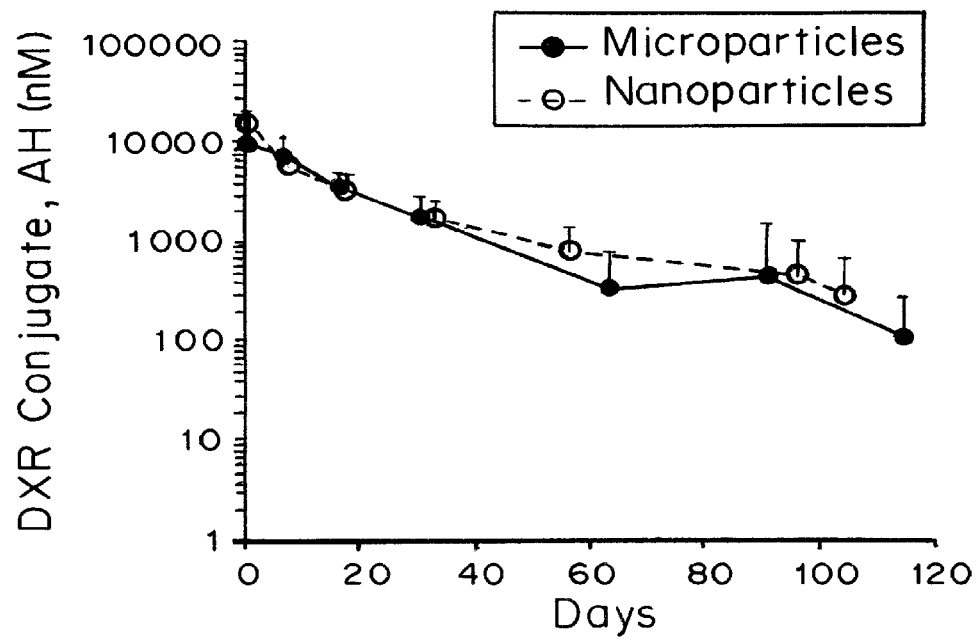
FIG. 7A is a graph showing the amount of drug conjugate released (nM) into the aqueous humor (AH) as a function of time (days) from microparticles and nanoparticles injected into the eyes of rabbits.

All rabbits displayed sustained drug release following intravitreal particle administration (FIG. 7A, Table 2).

Figure 7B:
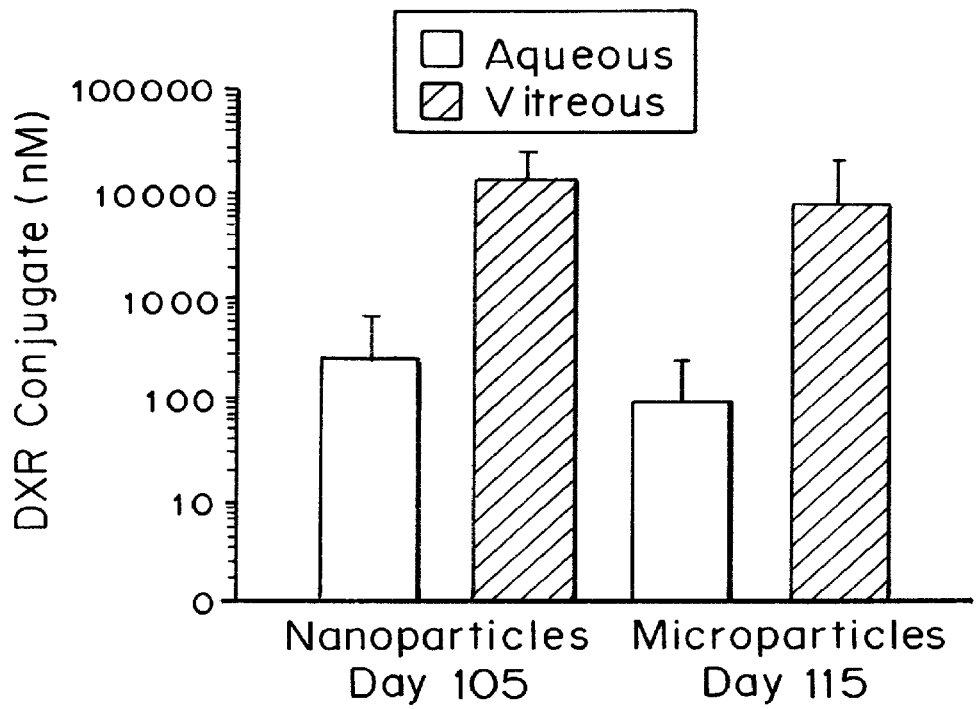
FIG. 7B is a bar graph that compares the amounts of released DXR drug conjugate (nM) in the aqueous humor (AH) and the vitreous of particle-injected rabbit eyes. The time (days) is 105 for the nanoparticle-treated animals and 115 for the microparticle-treated animals.

FIG. 7A is a graph showing the amount of released DXR drug conjugate (nM) as a function of time (days) in the aqueous humor (AH) of rabbits treated with microparticles and nanoparticles injected into the vitreous. FIG. 7B is a bar graph comparing the released drug amounts in the aqueous humor (AH) and vitreous of nanoparticle and microparticle-treated rabbits at days 105 and 115, respectively.

TABLE 3

Comparison of Released Drug Levels in the Aqueous Humor vs Vitreous

| | DXR concentration | | | | Ratio (uM) |
|---|---|---|---|---|---|
| | Aqueous Humor | | Vitreous | | |
| Treatment | ug/mL | uM | ug/mL | uM | Vitreous/Aqueous |
| Microparticles | | | | | |
| Rabbit 1 | 0.020 | 0.034 | 0.34 | 0.59 | 17 |
| Rabbit 2 | 0.184 | 0.317 | 17.50 | 30.17 | 95 |
| Rabbit 3 | 0.014 | 0.024 | 1.75 | 3.01 | 125 |
| Rabbit 4 | 0.030 | 0.052 | 0.79 | 1.37 | 27 |
| Rabbit 5 | 0.002 | 0.004 | 0.27 | 0.47 | 122 |
| Mean | 0.05 ± 0.08 | 0.09 ± 0.13 | 4.13 ± 7.50 | 7.12 ± 12.92 | 77 ± 52 |
| Nanoparticles | | | | | |
| Rabbit 1 | 0.10 | 0.17 | 4.81 | 8.30 | 50 |
| Rabbit 2 | 0.06 | 0.10 | 1.65 | 2.84 | 29 |
| Rabbit 3 | 0.45 | 0.77 | 17.32 | 29.86 | 39 |
| Rabbit 4 | 0.03 | 0.06 | 6.31 | 10.88 | 188 |
| Rabbit 5 | 0.03 | 0.05 | 4.44 | 7.66 | 144 |
| Mean | 0.13 ± 0.18 | 0.23 ± 0.31 | 6.91 ± 6.06 | 11.91 ± 10.45 | 90 ± 72 |

Data presented as mean ± SD.

TABLE 2

Pharmacokinetics of Intravitreal Delivery of DXR-PSA-PEG$_3$ Particles to Rabbits.

| DXR-PSA-PEG$_3$ Microparticles | | DXR-PSA-PEG$_3$ Nanoparticles | |
|---|---|---|---|
| Day | DXR Conc. in Aqueous Humor | Day | DXR Conc. in Aqueous Humor |
| 1 | 4 74 ± 2.23 µg/mL | 1 | 6.91 ± 2.40 µg/mL |
| 7 | 3.45 ± 1.76 µg/mL | 8 | 2.61 ± 1.11 µg/mL |
| 17 | 1.63 ± 0.65 µg/mL | 18 | 1.51 ± 0.77 µg/mL |
| 31 | 0.78 ± 0.52 µg/mL | 33 | 0.75 ± 0.41 µg/mL |
| 64 | 016 ± 0.21 µg/mL | 57 | 0.37 ± 0.27 µg/mL |
| 92 | 0.21 ± 0.45 µg/mL | 97 | 0.22 ± 0.26 µg/mL |
| 115 | 0.05 ± 0.08 µg/mL | 105 | 0.13 ± 0.18 µg/mL |

Data presented as mean ± SD.

Levels well above the limit of quantitation of the HPLC assay (10 ng/mL or 20 nM) were observed in both the microparticle and nanoparticle-treated animals for the duration of the study, 115 and 105 days, respectively (FIG. 7A). Direct comparison of the released drug levels in the AH compared to the vitreous revealed that vitreous levels were significantly higher than those measured in the AH, up to 188 times higher in the vitreous compared to the AH (Table 3, FIG. 7B). The mean released drug levels for the microparticle-treated animals at Day 115 were 0.09+0.13 uM in the AH and 7.12+12.92 uM in the vitreous. For the nanoparticle-treated animals at Day 105 mean released drug levels were 0.23+0.31 uM in the AH and 11.91+10.45 uM in the vitreous (Table 3). Drug levels in the vitreous were 77-90 times higher than drug levels measured in the AH.

Intravitreal delivery of DXR-PSA-PEG$_3$ micro or nanoparticles to rabbit eyes resulted in long-term drug release, sustained for at least 115 or 105 days, respectively, the duration of the study. The released drug levels measured in the vitreous where much higher than those measured in the aqueous humor, an average of 77-90-fold higher.

These data demonstrate sustained release from DXR-PSA-PEG$_3$ when delivered intraocularly and suggest that DXR-PSA-PEG$_3$ will be a promising therapy for the treatment of NV ocular diseases including NV AMD.

Example 4. Synthesis and In Vitro Evaluation of Fully Biodegradable DXR-PSA-PEG$_3$ Rods Rod-shaped DXR-PSA-PEG$_3$ conjugates were successfully produced with a diameter of 0.5 mm, a length of 0.5 cm, and a mass of 1 mg, with three doxorubicin (DXR) drug loading levels, 10%, 30%, and 50%. DXR release in vitro demonstrated release sustained for at least 25 days with all three rod types.

Materials and Methods

Preparation of PEG$_3$-PSA Polymer (Polyethylene glycol)3-co-poly(sebacic acid)(PEG$_3$-PSA) was synthesized by melt condensation. Briefly, sebacic acid was refluxed in acetic anhydride to form sebacic acid prepolymer (Acyl-SA). Polyethylene glycol (PEG$_3$) was prepared by mixing CH$_3$O-PEG-NH$_2$ (2.0 g), citric acid (26 g), dicyclohexylcarbodiimide (DCC; 83 mg) and 4-(dimethylamino)pyridine (DMAP, 4.0 mg) which were added to 10 mL methylene chloride, stirred overnight at room temperature, then precipitated and washed with ether, and dried under vacuum. Next, Acyl-SA (90% w/w) and PEG$_3$ (10% w/w) were polymerized at 180° C. for 30 minutes. Nitrogen gas was swept into the flask for 30 seconds every 15 minutes.

Polymers were cooled to ambient temperature, dissolved in chloroform and precipitated into excess petroleum ether. The precipitate was collected by filtration and dried under vacuum to constant weight, to produce the $PEG_3$-PSA polymer.

Preparation of DXR-PSA-$PEG_3$ Rods

To prepare DXR-PSA-$PEG_3$ rods, three different concentrations of DXR were used to produce rods with drug loading levels of 10%, 30% and 50% (w/w). For the 10%, 30% and 50% drug loaded rods, $PEG_3$-PSA and doxorubicin hydrochloride (DXR) (NetQem LLC, Durham, N.C.) were added to $CHCl_3$ at ratios of 9:1, 7:3, and 1:1 (w/w). The $PEG_3$-PSA and DXR were incubated at 50° C. for one hour after which the $CHCl_3$ was removed by vacuum. The reaction product was grated to a fine powder and then compressed into a glass tube, with a diameter of 0.5 mm, which was used as a mold. The rods were extruded from the mold and cut to 0.5 cm lengths. Each rod weighed approximately 1 mg (0.9-1.2 mg).

In Vitro Drug Release

One rod (~1 mg) was added to 1 ml of phosphate buffered saline (PBS, pH 7.4) and incubated at 37° C. on a rotating platform (140 RPM). At selected time points, supernatant was collected and fresh PBS added. DXR-conjugate concentration was measured by absorbance at 480 nm.

Results

Rod-shaped DXR-PSA-$PEG_3$ conjugates were produced with three different drug loading levels, 10%, 30%, and 50%. The DXR-PSA-$PEG_3$ conjugates were formed into rods with a diameter of 0.5 mm, a length of 0.5 cm, and a mass of 1 mg.

Figure 8:
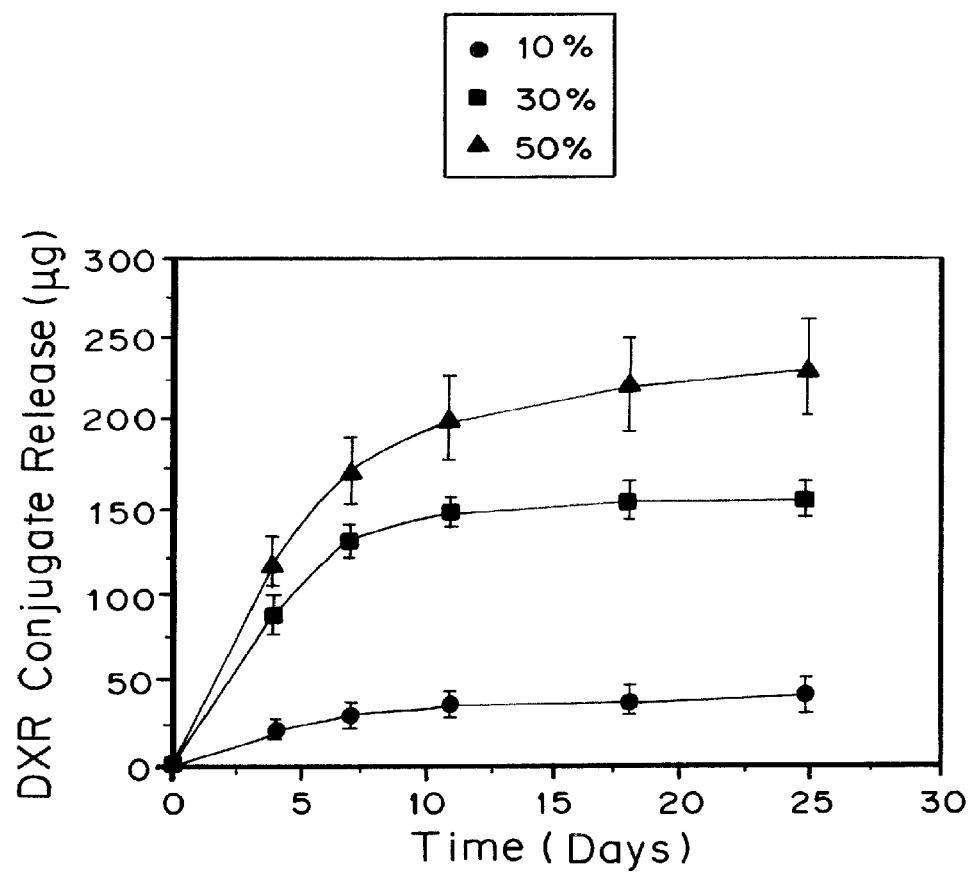
FIG. 8 is a graph showing release of doxorubicin (DXR) conjugate in vitro (m) as a function of time (days) for polymer rods containing 10% DXR (●), 30% DXR (■) and 50% DXR (▲).

The duration of in vitro drug release was evaluated using the DXR-PSA-$PEG_3$ rods, with drug loading levels of 10%, 30%, and 50% (FIG. 8). Drug release from all three rods was sustained for at least 25 days.

These data demonstrate that the synthesis of rod-shaped DXR-PSA-$PEG_3$ conjugates is possible. Rods composed of DXR-PSA-$PEG_3$ conjugates with different drug concentrations were successfully synthesized, and all rods displayed sustained drug release in vitro. These data also suggest that rods of differing sizes, mass, and drug content can be produced and drug release rates optimized to obtain the most efficacious drug delivery profile for each delivered drug and for each therapeutic indication.

Example 5. Production of DXR-PCPH-PSA-$PEG_3$ Polymer Conjugates

Microparticles composed of a fully biodegradable DXR-PSA-PCPH-$PEG_3$ polymer drug conjugate were synthesized and displayed a slower drug release rate and more sustained drug release duration compared to the DXR-PSA-$PEG_3$ microparticles. The addition of PCPH to the polymer increased the hydrophobicity of polymer-drug conjugate which resulted in a prolonged the duration of drug release, presumably due to a reduction in DXR solubility.

Materials and Methods

Synthesis of 1,6-bis(p-carboxyphenoxy)hexane (CPH)

1,6-bis(p-carboxyphenoxy)hexane (CPH) was synthesized as described by Conix (1966). Briefly, p-hydroxybenzoic acid (27.6 g) and sodium hydroxide (16.0 g) in water (80 mL) were stirred and heated to reflux temperature. 1,6-dibromohexane (96%, 15.7 mL) was added over a period of 30 min while maintaining at reflux temperature and refluxed for an additional 3.5 hours. Sodium hydroxide (4.0 g) dissolved in water (10 mL) was added to the mixture and refluxed for another 2 hours before allowing the reaction mixture to stand overnight at room temperature. The disodium salt was isolated by filtration, washed with 40 mL of methanol, and dissolved in distilled water. The solution was warmed to 60-70° C. and acidified with 6 N sulfuric acid. The dibasic acid was isolated by filtration and dried to constant weight under vacuum.

Synthesis of PreCPH 1,6-bis(p-carboxyphenoxy)hexane (CPH) (10.0 g) was refluxed in 200 mL of acetic anhydride for 30 min under nitrogen, followed by removal of unreacted diacid by filtration and solvent by evaporation. The residue was recrystallized from dimethylformamide and ethyl ether, washed with dry ethyl ether, and dried to constant weight under vacuum.

Synthesis of $PEG_3$-PSA-PCPH Prepolymer (Polyethylene glycol)$_3$-co-poly(sebacic acid)co-poly (CPH) ($PEG_3$-SA-PCPH) was synthesized by melt condensation. Briefly, sebacic acid was refluxed in acetic anhydride to form sebacic acid prepolymer (Acyl-SA). Polyethylene glycol ($PEG_3$) was prepared by mixing $CH_3O$-PEG-$NH_2$ (2.0 g), citric acid (26 g), dicyclohexylcarbodiimide (DCC; 83 mg) and 4-(dimethylamino)pyridine (DMAP, 4.0 mg) which were added to 10 mL methylene chloride, stirred overnight at room temperature, then precipitated and washed with ether, and dried under vacuum. Next, $PEG_3$ (10% w/v), acyl-SA (60% w/v), and preCPH (30% w/v), were polymerized at 180° C. for 30 minutes. Nitrogen gas was swept into the flask for 30 seconds every 15 minutes. Polymers were cooled to ambient temperature, dissolved in chloroform and precipitated into excess petroleum ether. The precipitate was collected by filtration and dried under vacuum to constant weight, to produce the $PEG_3$-PSA-PCPH prepolymer.

Preparation of DXR-PSA-PCPH-$PEG_3$ Microparticles

To prepare DXR-PSA-PCPH-$PEG_3$ microparticles, 200 mg $PEG_3$-PSA-PCPH was dissolved in 3 mL dichloromethane (DCM) and mixed with 40 mg doxorubicin hydrochloride (DXR) (NetQem LLC, Durham, N.C.) dissolved in 1.5 mL DMSO. Following incubation at 50° C. for 30 min, the mixture was homogenized in 100 mL of PVA at 3,000 rpm for 1 min. After stirring for 2 hr, particles were collected by centrifugation (9,000×g for 25 minutes) and washed thrice before lyophilization.

Particle Characterization

Particle size was determined using a Coulter Multisizer IV (Beckman-Coulter Inc., Fullerton, Calif.). Greater than 100,000 particles were sized for each batch of microparticles to determine the mean particle diameter.

In Vitro Drug Release

DXR-PSA-PCPH-$PEG_3$ microparticles (2 mg) were suspended in phosphate buffered saline (PBS, pH 7.4), and incubated at 37° C. on a rotating platform (140 RPM). At selected time points, supernatant was collected by centrifugation (13,500×g for 5 min) and particles were resuspended in fresh PBS. DXR-conjugate was measured by absorbance at 480 nm.

Results

DXR-PSA-PCPH-$PEG_3$ microparticles were synthesized and displayed a mean size of 24.3±8.7 um with a drug loading level of 13.9%.

Figure 9A:
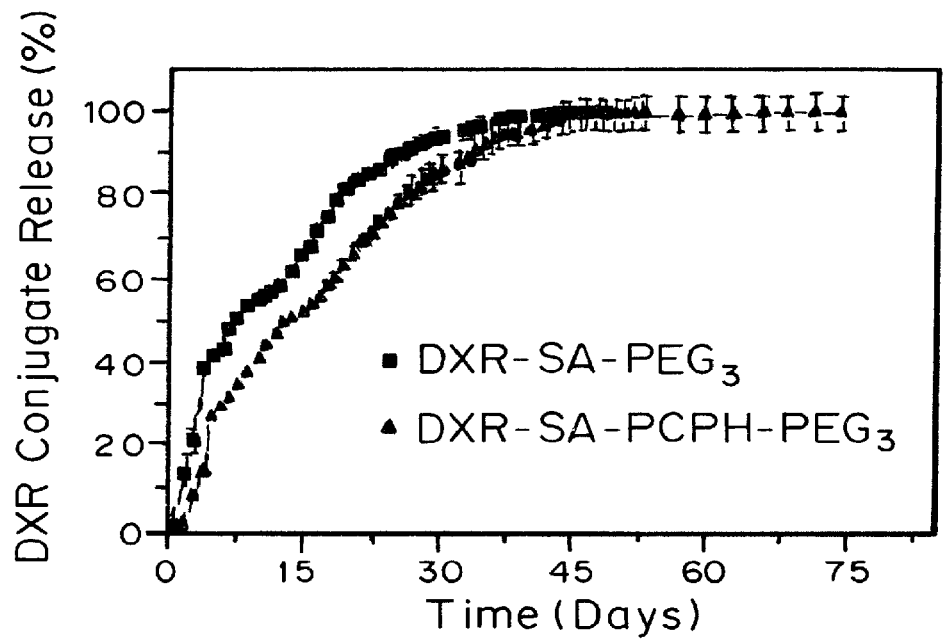
FIG. 9A is a graph showing the in vitro release profile of doxorubicin (DXR) conjugate from microparticles prepared from DXR-SA-PEG$_3$(■) and DXR-SA-CPH-PEG (▲).
Figure 9B:
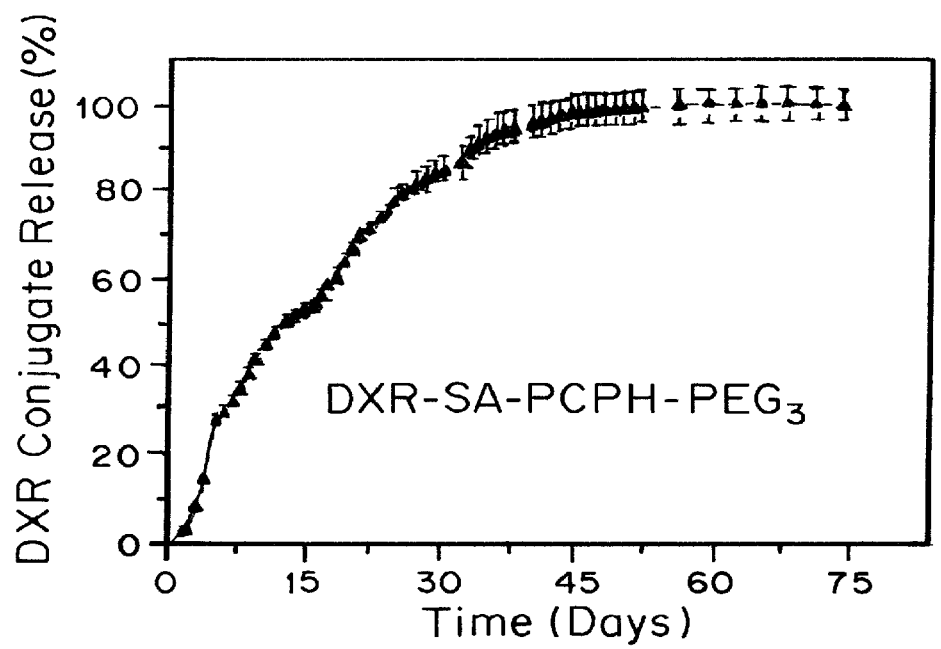
FIG. 9B is a graph showing the in vitro release profile of doxorubicin (DXR) conjugate from microparticles prepared from DXR-SA-CPH-PEG$_3$ (▲).

The duration of in vitro drug release was compared between the DXR-PSA-PCPH-$PEG_3$ microparticles and the DXR-PSA-$PEG_3$ microparticles (mean size 22.5+8.3 um). The DXR-PSA-$PEG_3$ microparticles showed drug release sustained for 45 days while the DXR-PSA-PCPH-$PEG_3$ microparticles demonstrated a slower drug release rate and drug release sustained for over 75 days (FIG. 9).

Microparticles composed of a fully biodegradable DXR-PSA-PCPH-PEG$_3$ polymer drug conjugate were synthesized. The DXR-PSA-PCPH-PEG$_3$ microparticles displayed a slower drug release rate and more sustained drug release duration compared to the DXR-PSA-PEG$_3$-microparticles, particles lacking the addition of the CPH polymer. The addition of CPH to the polymer increased the hydrophobicity of the released drug conjugate which is expected to reduce the solubility of DXR, and resulted in a prolonged duration of drug release.

These data demonstrate that by altering the polymer chemistry to increase the hydrophobicity of the released drug conjugate, the level and duration of drug release can be modified, indicating that these parameters can be optimized to obtain the most efficacious drug delivery profile for each delivered drug and for each therapeutic indication.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A polymer conjugate of the formula

wherein

A is an ophthalmic drug for treatment of the posterior segment of the eye selected from brimonidine, apraclonidine, brinzolamide, acetazolamine, dorzolamide, timolol, and carteolol;

Z is a hydrophilic polymer segment wherein the segment is poly(ethylene glycol);

Y is a multivalent branch point that is an organic, inorganic, or organometallic moiety;

X is a hydrophobic polymer segment wherein the segment is selected from a poly(lactic acid) segment, a poly(glycolic acid) segment, and a poly(lactic-co-glycolic acid) segment; and m and n are independently selected from 1, 2, 3, 4, and 5.

2. The polymer conjugate of claim 1, wherein m is 1 and n is 1.

3. The polymer conjugate of claim 1, wherein Y is selected from

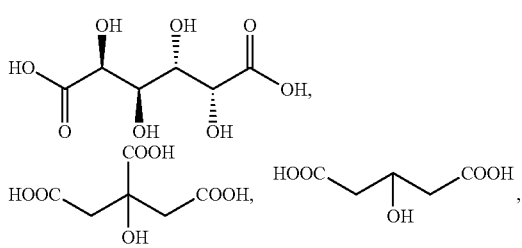

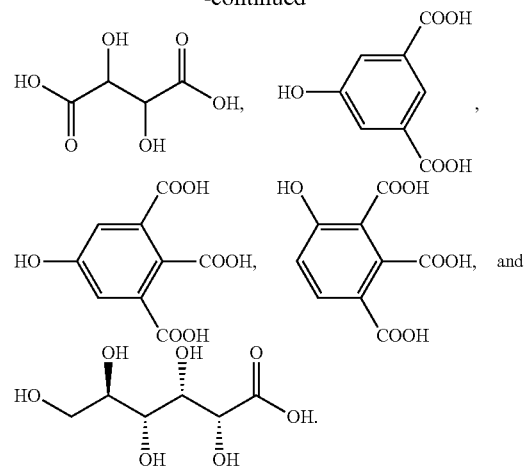

4. The polymer conjugate of claim 1, wherein X is a poly(lactic acid) segment.

5. The polymer conjugate of claim 4, wherein A is brimonidine.

6. The polymer conjugate of claim 4, wherein A is apraclonidine.

7. The polymer conjugate of claim 4, wherein A is brinzolamide.

8. The polymer conjugate of claim 4, wherein A is acetazolamine.

9. The polymer conjugate of claim 4, wherein A is dorzolamide.

10. The polymer conjugate of claim 1, wherein X is a poly(glycolic acid) segment.

11. The polymer conjugate of claim 10, wherein A is brimonidine.

12. The polymer conjugate of claim 10, wherein A is apraclonidine.

13. The polymer conjugate of claim 10, wherein A is brinzolamide.

14. The polymer conjugate of claim 10, wherein A is acetazolamine.

15. The polymer conjugate of claim 10, wherein A is dorzolamide.

16. The polymer conjugate of claim 1, wherein X is a poly(lactic-co-glycolic acid) segment.

17. The polymer conjugate of claim 16, wherein A is brimonidine.

18. The polymer conjugate of claim 16, wherein A is apraclonidine.

19. The polymer conjugate of claim 16, wherein A is brinzolamide.

20. The polymer conjugate of claim 16, wherein A is acetazolamine.

21. The polymer conjugate of claim 16, wherein A is dorzolamide.

22. A pharmaceutical composition containing microparticles comprising the polymer conjugate of claim 1 and a pharmaceutically acceptable excipient.

23. A method of treating a disease or disorder of the eye selected from wet-age related macular degeneration, choroidal neovascularization, glaucoma, corneal neovascularization, and retinal neovascularization comprising administering to a patient in need thereof the pharmaceutical composition of claim 22.

24. The method of claim 23, wherein the pharmaceutical composition is administered via intravitreal injection, subconjunctival injection, intracameral injection, intrastromal injection, intracorneal injection, subretinal injection, or intraocular injection.

25. The method of claim 24, wherein the pharmaceutical composition is administered via intravitreal injection.

26. The method of claim 24, wherein the pharmaceutical composition is administered via subconjunctival injection.

* * * * *

UNITED STATES PATENT AND TRADEMARK OFFICE
CERTIFICATE OF CORRECTION

PATENT NO. : 10,933,144 B2
APPLICATION NO. : 16/182261
DATED : March 2, 2021
INVENTOR(S) : Jie Fu, Peter A. Campochiaro and Justin Scot Hanes Page 1 of 1

It is certified that error appears in the above-identified patent and that said Letters Patent is hereby corrected as shown below:

In the Specification

Column 1, Lines 17-23, replace "This invention was made with Government Support under Agreements R01CA140746, P30EY001765, and U54CA151838 awarded to Justin Scot Hanes by the National Institutes of Health, and under agreement R01EY012609 awarded to Peter Anthony Campochiaro by the National Institutes of Health. The Government has certain rights in the invention." with --This invention was made with government support under CA140746, EY001765, CA151838, and EY012609 awarded by the National Institutes of Health. The government has certain right in the invention.--

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*